United States Patent
Coppeta et al.

(10) Patent No.: US 8,911,426 B2
(45) Date of Patent: Dec. 16, 2014

(54) LOW-PERMEABILITY, LASER-ACTIVATED DRUG DELIVERY DEVICE

(75) Inventors: Jonathan Robert Coppeta, Windham, NH (US); Kenneth N. Horne, San Francisco, CA (US); John T. Santini, Jr., North Chelmsford, MA (US); John A. Scholl, San Ramon, CA (US); Gregory J. R. Spooner, San Francisco, CA (US); Cynthia L. Stevenson, Mountain View, CA (US); Naveed Shams, Danville, CA (US); Andrew Poutiatine, Mill Valley, CA (US)

(73) Assignee: On Demand Therapeutics, Inc., Tyngsboro, MA (US)

( * ) Notice: Subject to any disclaimer, the term of this patent is extended or adjusted under 35 U.S.C. 154(b) by 740 days.

(21) Appl. No.: 13/023,370

(22) Filed: Feb. 8, 2011

(65) Prior Publication Data
US 2012/0035528 A1   Feb. 9, 2012

Related U.S. Application Data

(60) Provisional application No. 61/330,811, filed on May 3, 2010, provisional application No. 61/302,387, filed on Feb. 8, 2010.

(51) Int. Cl.
| | | |
|---|---|---|
| *A61K 9/22* | (2006.01) | |
| *A61K 9/00* | (2006.01) | |
| *A61F 9/00* | (2006.01) | |
| *A61F 9/008* | (2006.01) | |

(52) U.S. Cl.
CPC ............. *A61F 9/0017* (2013.01); *A61K 9/0051* (2013.01); *A61K 9/0009* (2013.01); *A61F 9/008* (2013.01)
USPC .......................... 604/890.1; 604/19; 424/422

(58) Field of Classification Search
CPC . A61M 31/002; A61K 9/0009; A61K 9/0097; A61K 9/4808; A61F 2250/0067; A61F 2250/0068
USPC ......... 604/19, 20, 890.1, 891.1; 424/422–437
See application file for complete search history.

(56) References Cited

U.S. PATENT DOCUMENTS

| | | |
|---|---|---|
| 4,509,880 A | 4/1985 | Wamstad |
| 4,702,228 A | 10/1987 | Russell, Jr. et al. |

(Continued)

FOREIGN PATENT DOCUMENTS

| | | |
|---|---|---|
| WO | 2009/097468 A2 | 8/2009 |
| WO | 2009/097468 A3 | 10/2009 |

OTHER PUBLICATIONS

Horne, et al., U.S. Appl. No. 12/910,572, filed Oct. 22, 2010, titled as,"Providing a Visual Indication of Rupture or a Drug Reservoir Implanted within an Eye".

(Continued)

*Primary Examiner* — Kami A Bosworth
(74) *Attorney, Agent, or Firm* — Sutherland Asbill & Brennan LLP

(57) ABSTRACT

An implantable drug delivery device that uses multiple reservoir elements to contain and release doses of active pharmaceutical ingredients. The device includes a first shell element, which has a first enclosed cavity volume and forms a low-permeability barrier. The first shell element is configured to absorb light irradiation from a laser source, the laser irradiation causing a breach in the first shell element. A first active pharmaceutical ingredient is contained in the first enclosed cavity volume and is released when the first shell element is breached. The device also includes a second shell element, which has a second enclosed cavity volume and also forms a low-permeability barrier. A second active pharmaceutical ingredient is contained in the second enclosed cavity volume. The device also includes an envelope element containing the first and second shell elements.

16 Claims, 29 Drawing Sheets

(56) References Cited

U.S. PATENT DOCUMENTS

| | | | |
|---|---|---|---|
| 4,784,116 | A | 11/1988 | Russell, Jr. et al. |
| 5,378,475 | A | 1/1995 | Smith et al. |
| 5,797,898 | A | 8/1998 | Santini, Jr. et al. |
| 6,080,099 | A | 6/2000 | Slater et al. |
| 6,217,895 | B1 | 4/2001 | Guo et al. |
| 6,403,916 | B1 | 6/2002 | Spooner et al. |
| 6,474,535 | B1 | 11/2002 | Shanks et al. |
| 6,537,192 | B1 | 3/2003 | Elliott et al. |
| 6,548,078 | B2 | 4/2003 | Guo et al. |
| 6,669,622 | B2 | 12/2003 | Reed et al. |
| 6,709,379 | B1 * | 3/2004 | Brandau et al. ................ 600/3 |
| 6,716,156 | B2 | 4/2004 | Menuhr et al. |
| 6,726,918 | B1 | 4/2004 | Wong et al. |
| 6,737,753 | B2 | 5/2004 | Kumar et al. |
| 6,808,522 | B2 | 10/2004 | Richards et al. |
| 6,827,250 | B2 | 12/2004 | Uhland et al. |
| 6,846,283 | B2 | 1/2005 | Green et al. |
| 6,899,717 | B2 | 5/2005 | Weber et al. |
| 6,976,982 | B2 | 12/2005 | Santini, Jr. et al. |
| 7,033,605 | B2 | 4/2006 | Wong |
| 7,114,312 | B2 | 10/2006 | Coppeta et al. |
| 7,226,442 | B2 | 6/2007 | Sheppard, Jr. et al. |
| 7,488,316 | B2 | 2/2009 | Prescott et al. |
| 7,497,846 | B2 | 3/2009 | Uhland et al. |
| 7,582,080 | B2 | 9/2009 | Santini, Jr. et al. |
| 7,625,582 | B2 | 12/2009 | Wong |
| 7,767,223 | B2 | 8/2010 | Wong |
| 7,776,024 | B2 | 8/2010 | Santini, Jr. et al. |
| 7,874,974 | B2 | 1/2011 | Terwilliger et al. |
| 2003/0203210 | A1 | 10/2003 | Graff et al. |
| 2004/0082937 | A1 * | 4/2004 | Ausiello et al. ........... 604/891.1 |
| 2004/0143236 | A1 | 7/2004 | Santini et al. |
| 2004/0247671 | A1 | 12/2004 | Prescott et al. |
| 2006/0115323 | A1 | 6/2006 | Coppeta et al. |
| 2007/0122483 | A1 | 5/2007 | Myers |
| 2007/0196682 | A1 | 8/2007 | Visser et al. |
| 2007/0275035 | A1 | 11/2007 | Herman et al. |
| 2008/0015494 | A1 | 1/2008 | Santini et al. |
| 2008/0071252 | A1 | 3/2008 | Santini et al. |
| 2008/0083041 | A1 | 4/2008 | Santini et al. |
| 2008/0172043 | A1 | 7/2008 | Sheppard et al. |
| 2008/0177153 | A1 | 7/2008 | Bachman et al. |
| 2008/0221555 | A1 | 9/2008 | Sheppard et al. |
| 2008/0221557 | A1 | 9/2008 | Santini et al. |
| 2009/0142386 | A1 | 6/2009 | Prescott et al. |
| 2009/0196903 | A1 * | 8/2009 | Kliman ........................ 424/423 |
| 2010/0119604 | A1 | 5/2010 | Prescott et al. |

OTHER PUBLICATIONS

Lipka, et al. "Biostability of Materials for an Implanted Drug Delivery Device", Annual Meeting—Society for Biomaterials in Conjunction with the International Biomaterials Symposium, 2006, 1 page.

Maloney, et al. "In Vivo Biostability of CVD Silicon Oxide and Silicon Nitride Films", Materials Research Society Symposium Proceedings, vol. 872, 2005, pp. J14.3.1-J14.3.6.

Proos, et al. "Long-term Stability and in vitro Release of hPTH(1?34) from a Multi-reservoir Array", Pharmaceutical Research, vol. 25, No. 6, Jun. 2008, pp. 1387-1395.

PCT Search Report and Written Opinion mailed Jun. 24, 2011 for PCT Application No. PCT/US2011/024074 (19 pages).

Invitation to Pay Additional Fees and Partial Search Report received for PCT Patent Application No. PCT/US2011/024074, mailed on Apr. 27, 2011, 5 pages.

* cited by examiner

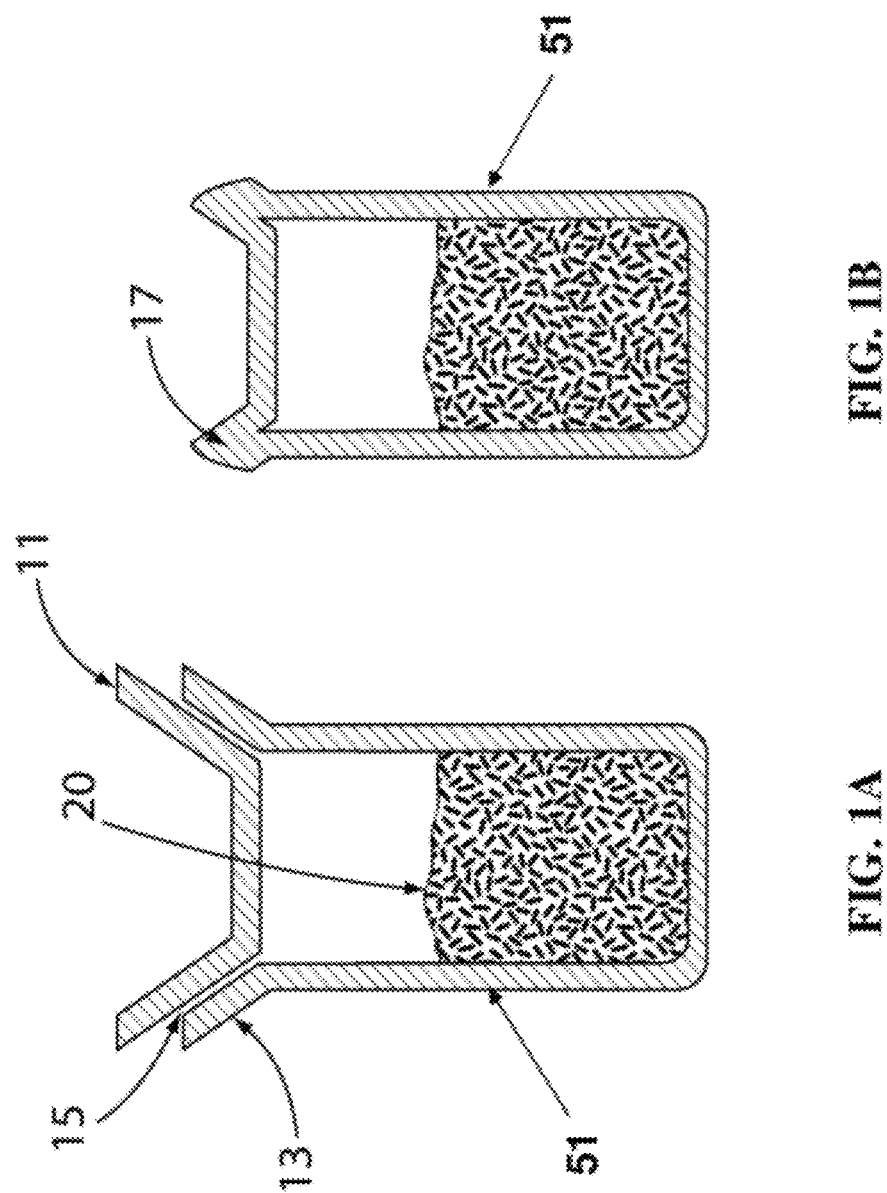

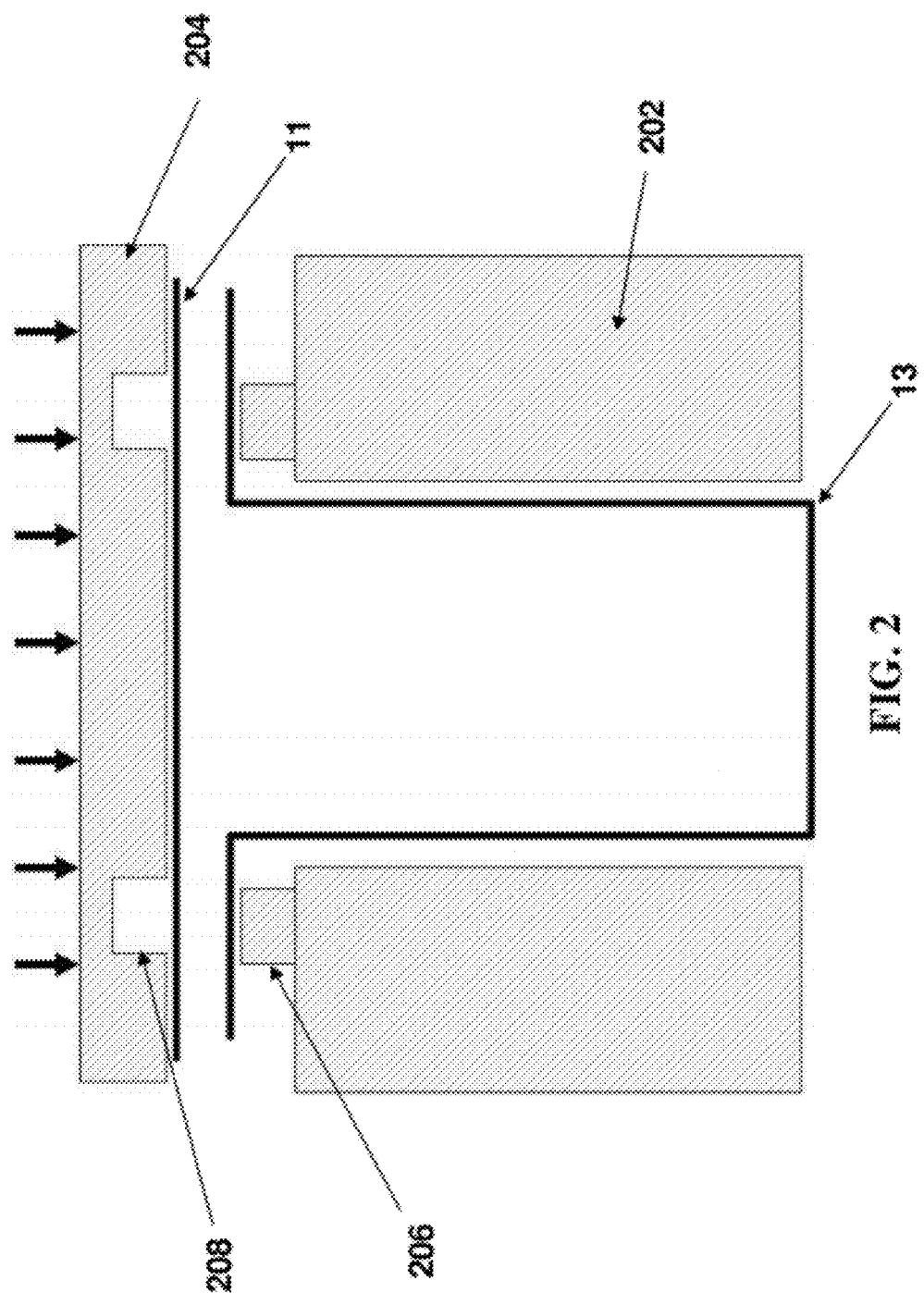

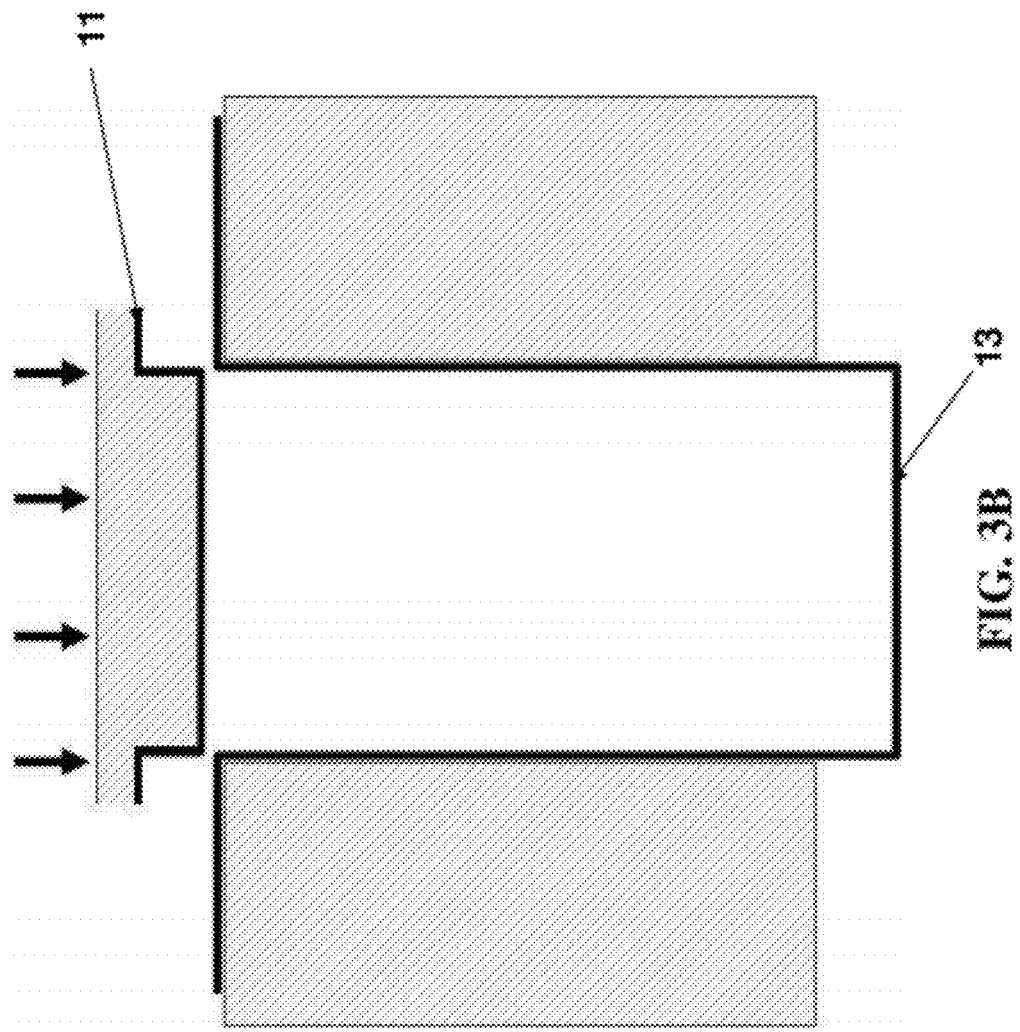

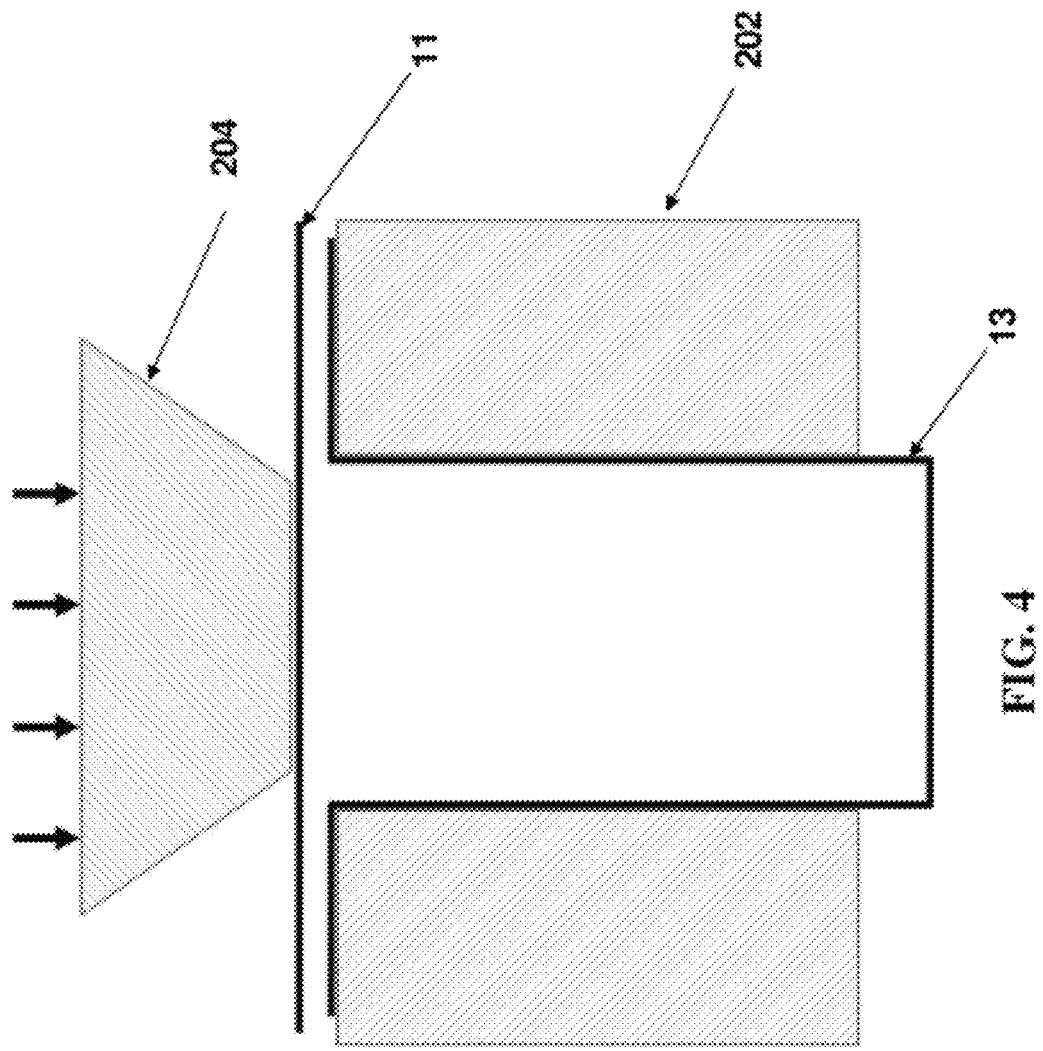

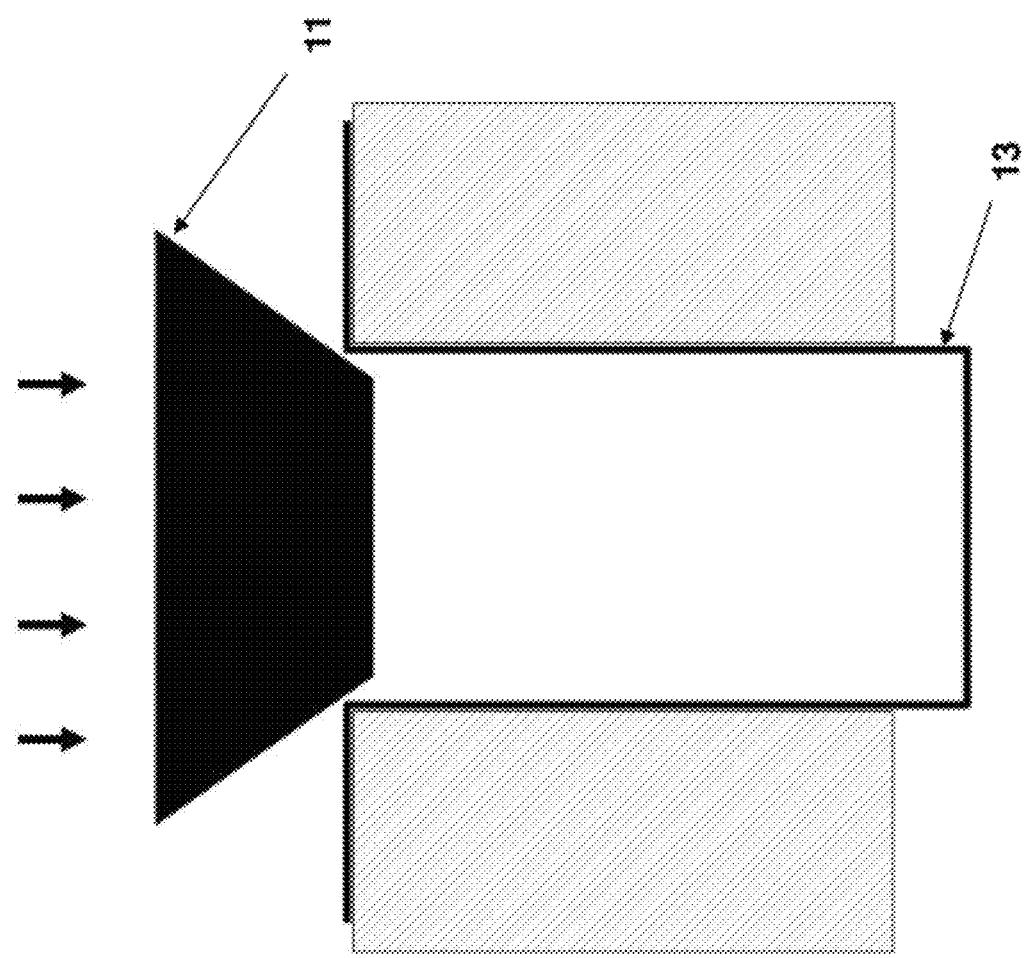

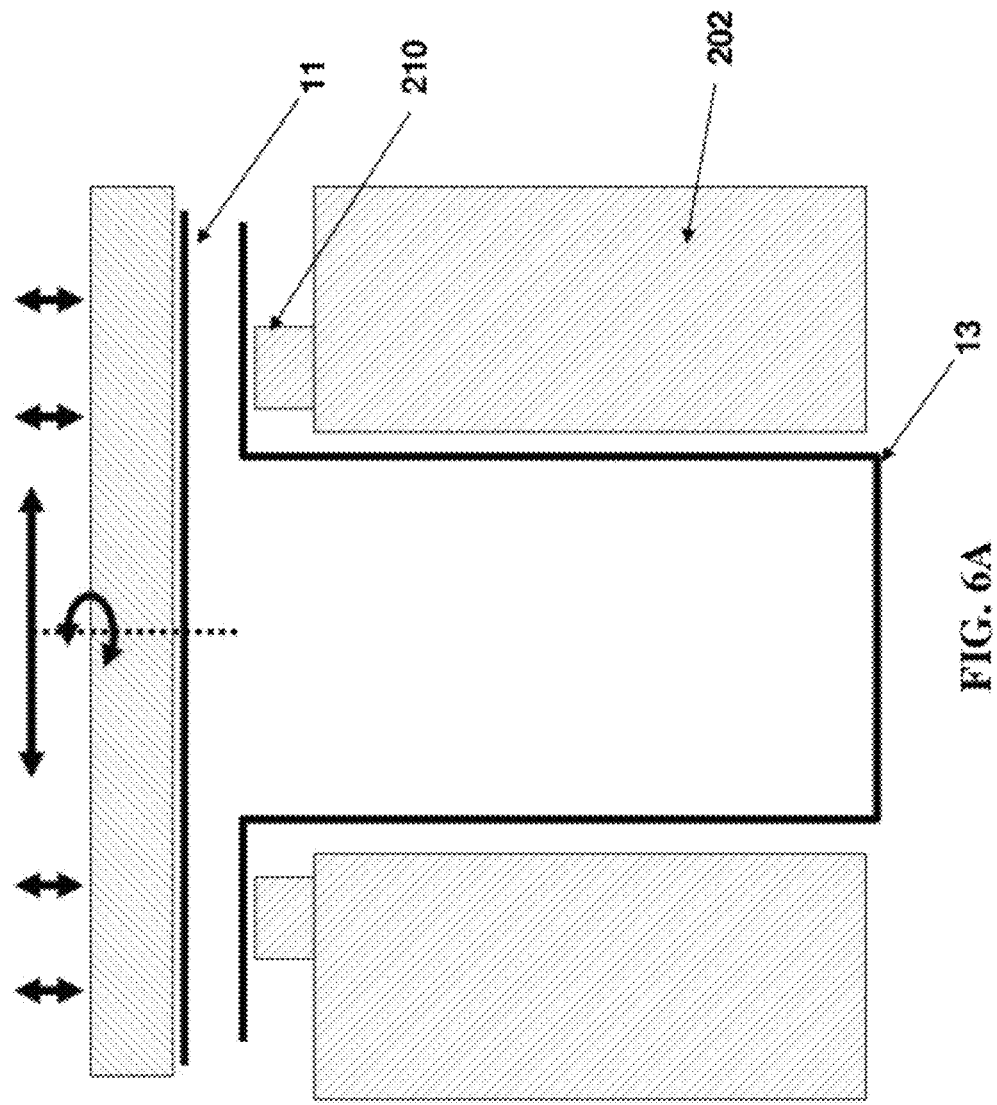

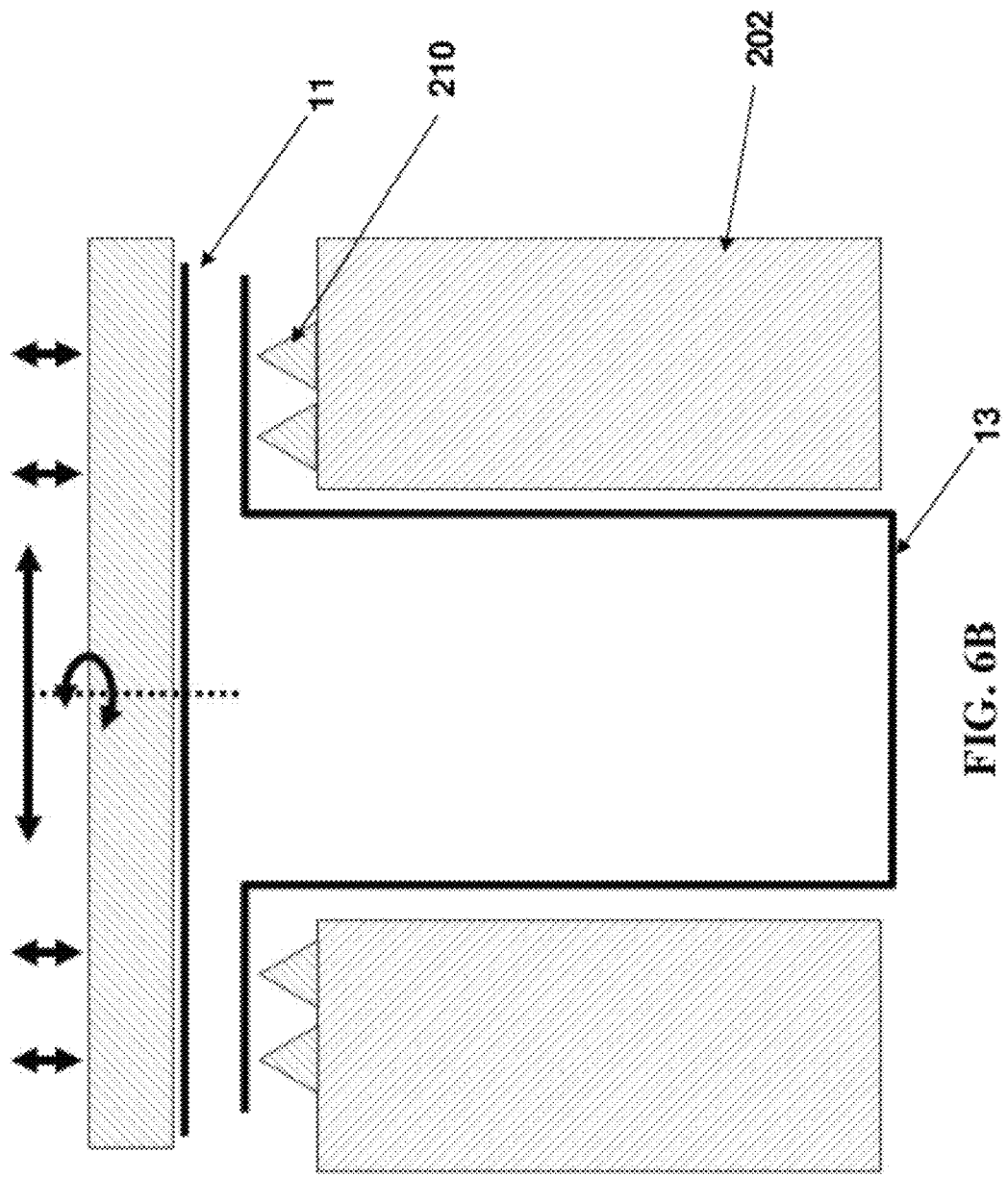

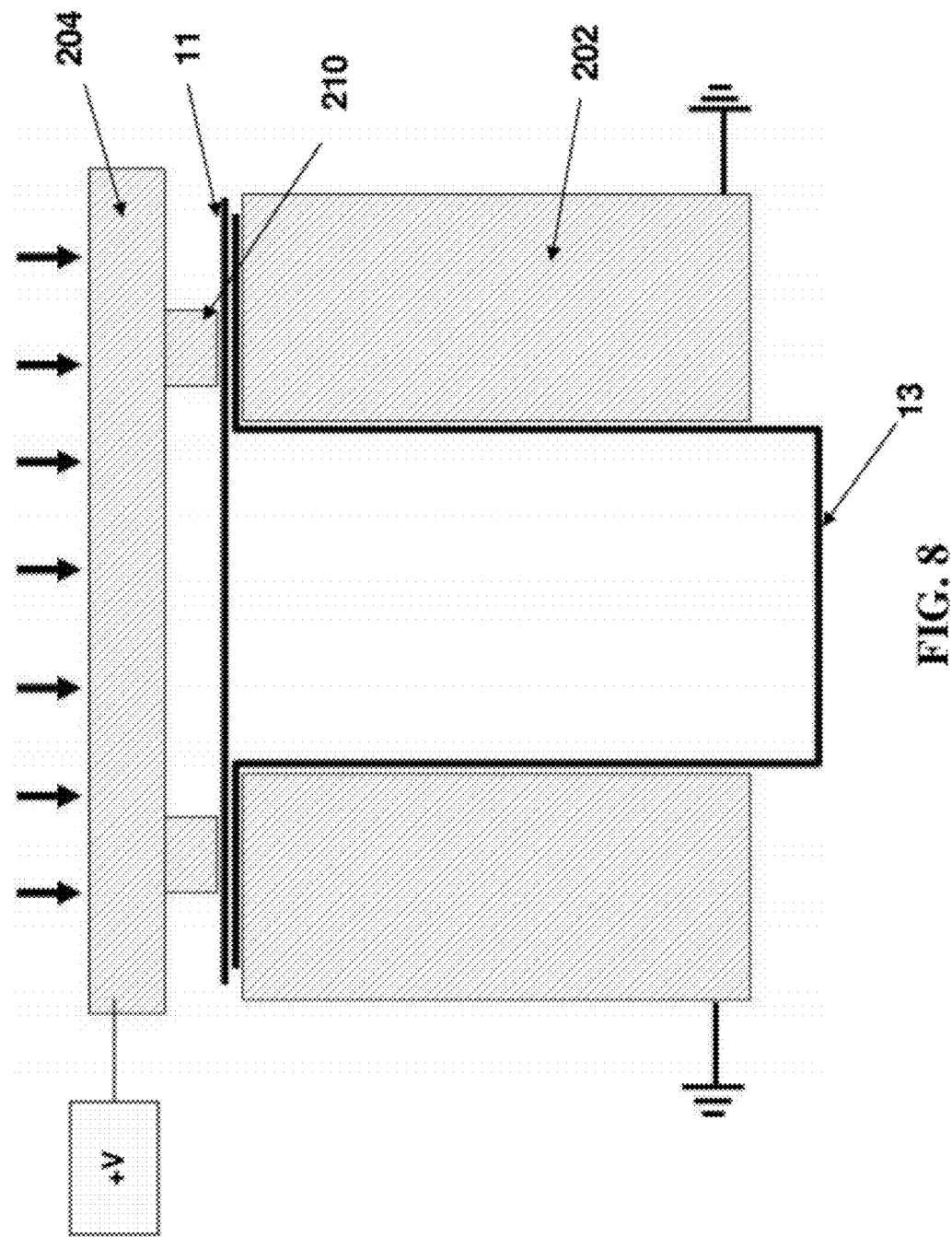

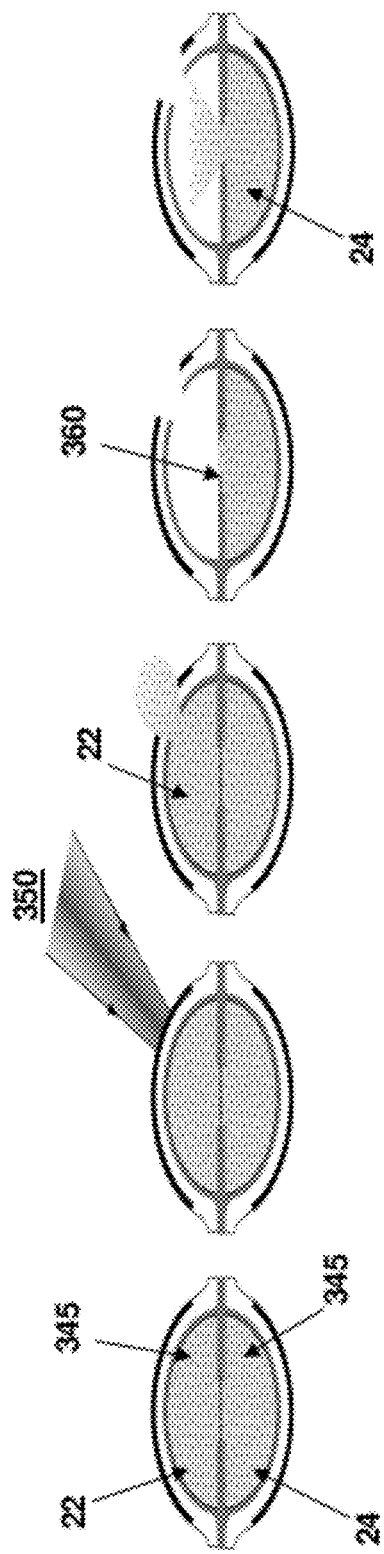

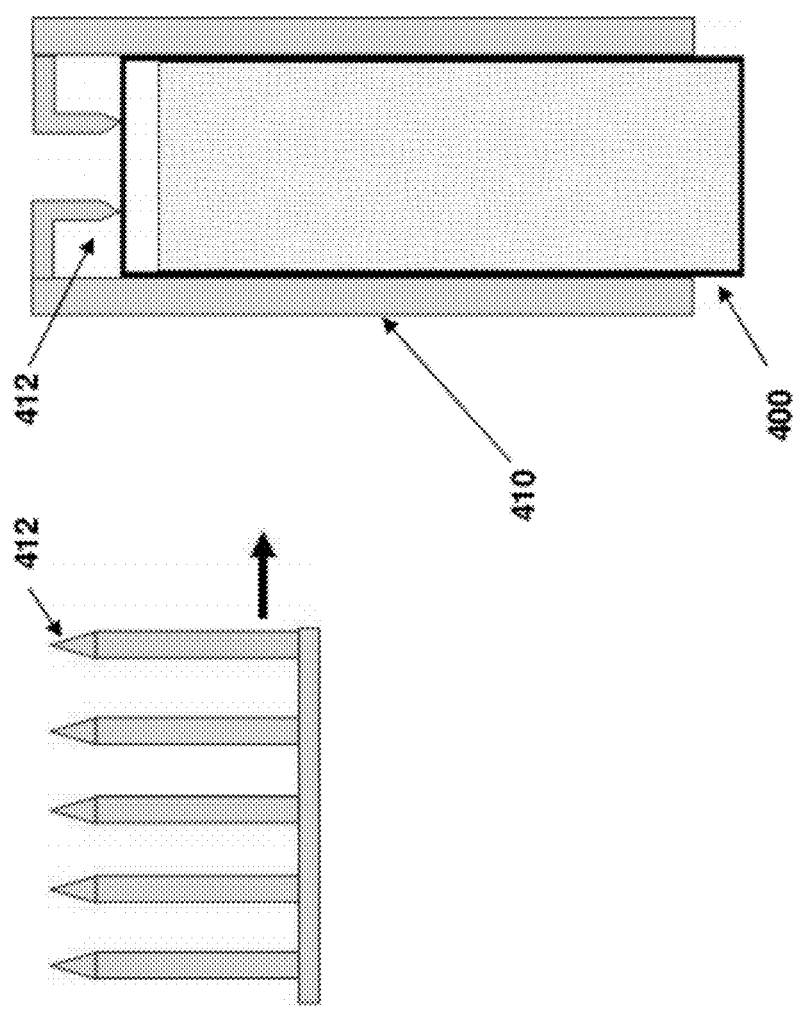

LOW-PERMEABILITY, LASER-ACTIVATED DRUG DELIVERY DEVICE

CROSS-REFERENCE TO RELATED APPLICATIONS

This application claims the priority benefit of U.S. provisional applications Ser. No. 61/330,811, filed May 3, 2010, and Ser. No. 61/302,387, filed Feb. 8, 2010, which are incorporated herein by reference in their entirety.

FIELD

The present disclosure is directed to implantable devices for laser-activated drug delivery and, in particular, low-permeability, laser-activated reservoirs used to deliver an active pharmaceutical ingredient to the interior of the eye for the treatment of ocular conditions.

BACKGROUND

The posterior chamber of the eye and, in particular, the retina and associated structures, are critical to vision. Significant vision threatening diseases are associated with these structures, including macular degeneration, diabetic retinopathy, diabetic macular edema, and central and branch vein retinal occlusion. The preferred treatment for many of these conditions is the delivery of an active pharmaceutical ingredient (API) directly to a portion of the eye. However, the anatomy and humor circulation system of the eye present a significant barrier to drug entry, particularly into the posterior chamber and vitreous portions of the eye.

One method of providing treatment to the eye is the injection of an API into the posterior chamber and vitreous portions of the eye. While simple and efficacious, serious side effects may result from repeated syringe needle invasion of the eye globe due to multiple injection treatments. The injection treatment method also limits the total dose that may be applied at a given time and restricts the pharmacokinetic profile that can be achieved. Finally, a disease management program that is based on frequent injections may not be practical or feasible. Multiple injection treatment requires that the patient visit a physician or ophthalmologist for each injection, which may become impractical and expensive for chronic conditions. Furthermore, due to resource constraints, it may be unfeasible for an ophthalmologist to facilitate multiple injection treatment for a large number of patients with chronic conditions.

As an alternative to or in addition to injection treatment, a drug-eluting device may be implanted directly into the eye. These devices are surgically implanted or are injected into the posterior chamber and include gancyclovir and steroid eluting drug components. Commercially available steroid eluting implants include fluocinolone acetonide implants (e.g., Retisert®, Vitrasert®, and Iluvien™) and dexamethasone implants (e.g., Ozurdex®). Typically, such implants release a drug at a constant or slowly changing rate. See, U.S. Pat. Nos. 6,217,895 and 6,548,078 (to Retisert), U.S. Pat. No. 5,378,475 (to Vitrasert), U.S. Pat. Nos. 6,726,918, 6,899,717, 7,033,605, 7,625,582, 7,767,223 (to Ozurdex), and U.S. Patent Pub. 2007/0122483 (to Iluvien), which are incorporated by reference. These implantable devices typically provide a constant pharmacokinetic profile resulting from a continuous drug dosing. This continuous dosing may be acceptable for certain drugs, but for other drugs, continuous dosing can result in serious side effects. For example, continuous delivery of a steroid in the eye results in a high incidence of cataracts or elevated intraocular pressure that may result in glaucoma. Thus, in some cases, it is desirable to reduce the incidence of these side effects by providing a treatment that delivers the drug only when needed.

Another significant challenge in the development of technologies for the delivery of pharmaceutical drugs and, in particular, macromolecule (e.g., peptide and protein) drugs, is the limited stability of these molecules when in contact with water or in an aqueous solution. Many macromolecule drugs, including proteins, that are unstable in aqueous solution are handled and stored as dry solids ("dry" is defined within this document as substantially free of residual moisture, typically with a water content not exceeding 10% water by weight). Delivery systems that store or release macromolecule drugs in liquid or gel form will have limited utility due to accelerated degradation of the drug caused by high residual moisture. If a macromolecule drug can be kept in a dry, solid form, its degradation can be minimized and a long-term implantable device is possible. See, Elizabeth R. Proos, James H. Prescott and Mark A. Staples "Long-term Stability and In Vitro Release of hPTH(1-34) from a Multi-reservoir Array" *Pharmaceutical Research*, Volume 25, Number 6, 1387-1395 (Feb. 12, 2008). It is therefore desirable to create a drug delivery system that stores a drug in a dry, solid form and that prohibits or limits any moisture from passing through the device and into the drug, until such time that release of the drug is desired.

Moisture transport into or out of a drug delivery device can be prohibited or limited through the use of a low-permeability barrier constructed using hermetic materials and the use of hermetic sealing techniques. Stability of a macromolecule drug may be increased if it is formulated with excipients that enhance or maintain the molecule's stability, if it is stored with its optimal residual moisture content, and if the residual moisture content is maintained with a hermetically-sealed barrier reducing the transport of water into or out of the drug formulation.

It is known that metallic films on silicon wafer wells to perform long-term sealing of APIs in an electro-thermally-activated drug delivery device (DDD). This approach allows for hermetic or highly impermeable DDDs. For example, see U.S. Pat. Nos. 6,976,982, 7,776,024, 7,582,080, 7,226,442, 6,808,522, 5,797,898, 7,488,316, 6,827,250, 7,114,312, and 7,497,846 and U.S. Pub. Nos. 2006/0115323 A1, 2008/0221557, 2008/0221555, 2008/0172043, 2008/0083041, 2008/0015494, 2008/0071252 A1, 2007/0275035 A1, 2009/0142386 A1, 2004/0247671 A1, and 2010/0119604 A1, assigned to MicroCHIPS, which are hereby incorporated by reference.

Thus, there is need for an implantable drug delivery device that provides a low-permeability barrier to protect a sensitive drug payload, and is also capable of laser activation so that a drug dosing can be initiated using noninvasive techniques.

SUMMARY

The devices and techniques described herein allow for the selective release of an API using laser irradiation of a hermetically-sealed reservoir or reservoirs. This is especially useful for devices that have been implanted in the transparent tissues of the eye, in which the non-invasive and efficacious introduction of a laser beam may be easily accomplished. Because the devices may be hermetically sealed, they are also highly impermeable to water, water vapor or reactive gases such as oxygen. Thus, these devices are capable of providing long-term viability for APIs that are sensitive to chemical change, such as, for example, degradation by moisture or oxygen.

The devices described herein use materials that are both capable of providing a low-permeability barrier and can be breached by laser irradiation.

One embodiment includes an implantable drug delivery device that uses multiple shell elements to contain and release doses of active pharmaceutical ingredients. The device includes a first shell element, which has a first enclosed cavity volume and forms a low-permeability barrier. The first shell element is configured to absorb light irradiation from a laser source, the laser irradiation causing a breach in the first shell element. A first active pharmaceutical ingredient is contained in the first enclosed cavity volume and is released when the first shell element is breached. The device also includes a second shell element, which has a second enclosed cavity volume and forms a low-permeability barrier. The second shell element is configured to absorb light irradiation from a laser source, the laser irradiation causing a breach in the second shell element. A second active pharmaceutical ingredient is contained in the second enclosed cavity volume and is released when the second shell element is breached. The device also includes an envelope element containing the first and second shell elements.

Another embodiment includes an implantable drug delivery device that uses multiple stacking reservoirs to contain and release doses active pharmaceutical ingredients. The device includes a first cup element having a cavity portion and an open end, and a bottom portion. The device also includes a second cup element having a cavity portion, an open end and a bottom portion. The bottom portion of the second cup element is configured to mate to the open end of the first cup element. The cavity portion of the first cup element and the bottom portion of the second cup element are joined with a mechanical bond to create a first enclosed cavity volume. The mechanical bond creates a low-permeability seal. The first cup element is configured to absorb light irradiation from a laser source, the light irradiation causing a breach in the first cup element. The device also includes an end cap element configured to mate to the open end of the second cup element. The cavity portion of the second cup element and the end cap element are mechanically joined to create a second enclosed cavity volume and to create a low-permeability barrier preventing moisture from entering the second enclosed cavity volume. The device also includes a first active pharmaceutical ingredient contained in the first enclosed cavity volume. The first active pharmaceutical ingredient is released when the cup element is breached. A second active pharmaceutical ingredient contained in the second enclosed cavity volume.

Another embodiment includes an implantable drug delivery device that uses multiple flanged cup reservoirs to contain and release doses active pharmaceutical ingredients. The device includes a cup element having an open end and a flange portion. An end cap element is mechanically joined to the flange portion of the cup element so as to create an enclosed cavity volume and to create a low-permeability seal preventing moisture from entering the enclosed cavity volume. An active pharmaceutical ingredient is contained in the enclosed cavity volume. The cup element is configured to absorb light irradiation from a laser source. The light irradiation causing a breach in the cup element, and the active pharmaceutical ingredient is released when the cup element is breached.

Another embodiment includes an implantable drug delivery device that uses a crimped tube to form multiple reservoirs to contain and release doses active pharmaceutical ingredients. An exemplary embodiment creates an implantable drug delivery device having multiple reservoir portions from a single tube element, the tube element having a closed end and an open end. A first active pharmaceutical ingredient dose is loaded into the tube element. A portion of the tube element is crimped and sealed proximate the open end to create a first reservoir portion containing the first active pharmaceutical ingredient. The first reservoir portion acts as a low-permeability barrier. A second active pharmaceutical ingredient dose is loaded into the tube element. A portion of the tube element is crimped and sealed to create a second reservoir portion containing the second active pharmaceutical ingredient. The second reservoir portion acts as a low-permeability barrier. The tube element is configured to absorb light irradiation from a laser source, the light irradiation causing a breach in the tube element. The first or second active pharmaceutical ingredient is released when the tube element is breached.

Another embodiment includes an implantable drug delivery device that uses an ampule reservoir to contain and release doses active pharmaceutical ingredients. The device includes a tube element having two open ends. The tube element is made from one of a glass or ceramic materials. The device also includes a first end cap element mechanically joined to one of the open ends of the tube element and a second end cap element mechanically joined to the other open end of the tube element. The tube element, first end cap element, and second end cap element create an enclosed cavity volume. The mechanical joining of the tube, first end cap, and second end cap creates a low-permeability seal preventing moisture from entering the enclosed cavity volume. The tube element is also configured to absorb light irradiation from a laser source, the light irradiation causing cause a breach in the tube element. An active pharmaceutical ingredient is contained in the enclosed cavity volume and is released when the tube element is breached.

In some embodiments, the implantable drug delivery device has an insertion profile less than 0.5 mm and can be implanted into the eye by intravitreal injection. In some embodiments, the active pharmaceutical ingredient is protected from ingress of water or air when implanted in the eye for a period of at least 30 days.

In some embodiments, the laser irradiation includes an application of energy from a laser. The laser is selected from the group consisting of an argon ion laser, a Nd:YAG laser, a frequency-doubled Nd:YAG laser, a diode laser, a Nd:YLF laser, a frequency-doubled Nd:YLF laser, a krypton ion laser, a dye laser, and a helium-neon laser, a Raman-shifted Nd:YAG, a Nd:YVO4 (vandate) laser, a frequency doubled Nd:YAG, Nd:YVO4 (vandate) laser, a Raman-shifted Yb:fiber, a Yb:glass and Yb:YAG laser, a frequency doubled Yb:fiber, Yb:glass and Yb:YAG, and other non-linear optics crystal wavelength shifted lasers, including; frequency doubled VECSELs, sum and difference frequency mixed laser outputs from NIR lasers such as Nd:YVO4, Nd:YAG, using such crystals as BBO, LBO, CLBO, KTP, KD*P, and RTA.

In some embodiments the active pharmaceutical ingredient comprises one or more of the group consisting of: anti-angiogenesis agents, anti-inflammatories, anti-infectives, anti-allergens, cholinergic agonists and antagonists, adrenergic agonists and antagonists, anti-glaucoma agents, agents for cataract prevention or treatment, neuroprotection agents, anti-oxidants, antihistamines, anti-platelet agents, anti-coagulants, anti-thrombic agents, anti-scarring agents, anti-proliferatives, anti-tumor agents, complement inhibitors, decongestants, vitamins, growth factors, anti-growth factor agents, gene therapy vectors, chemotherapy agents, protein kinase inhibitors, small interfering RNAs, antibodies, antibody fragments, fusion proteins, limus family compounds, and combinations thereof. In some embodiments, the anti-growth factor agent is an anti-vascular endothelial growth factor (anti-VEGF) agent. In some embodiments, the anti-VEGF agent is selected from the group consisting of aflibercept (VEGF trap), bevacizumab (AVASTIN), pegaptanib sodium (MACUGEN), and ranibizumab (LUCENTIS).

BRIEF DESCRIPTION OF THE DRAWINGS

FIGS. 1A and 1B depict exemplary flanged metallic reservoirs, before and after sealing.

FIG. 2 depicts an exemplary cold-welded flanged metallic reservoir.

FIGS. 3A and 3B depict exemplary cold-welded flanged metallic reservoirs.

FIG. 4 depicts an exemplary cold-welded flanged metallic reservoir using a tapered plug fixture.

FIG. 5 depicts an exemplary cold-welded flanged metallic reservoir using a metal plug.

FIGS. 6A and 6B depict exemplary ultrasonic-welded flanged metallic reservoirs.

FIG. 8 depicts an exemplary resistive-welded flanged metallic reservoir.

FIG. 23 depicts a polymer-metal laminate reservoir with an erodible barrier between API cakes in a multi-chamber reservoir, after sealing and during laser-activated breach.

FIG. 27 depicts an embodiment for indirect breach of a reservoir

DETAILED DESCRIPTION

Figure 3A:
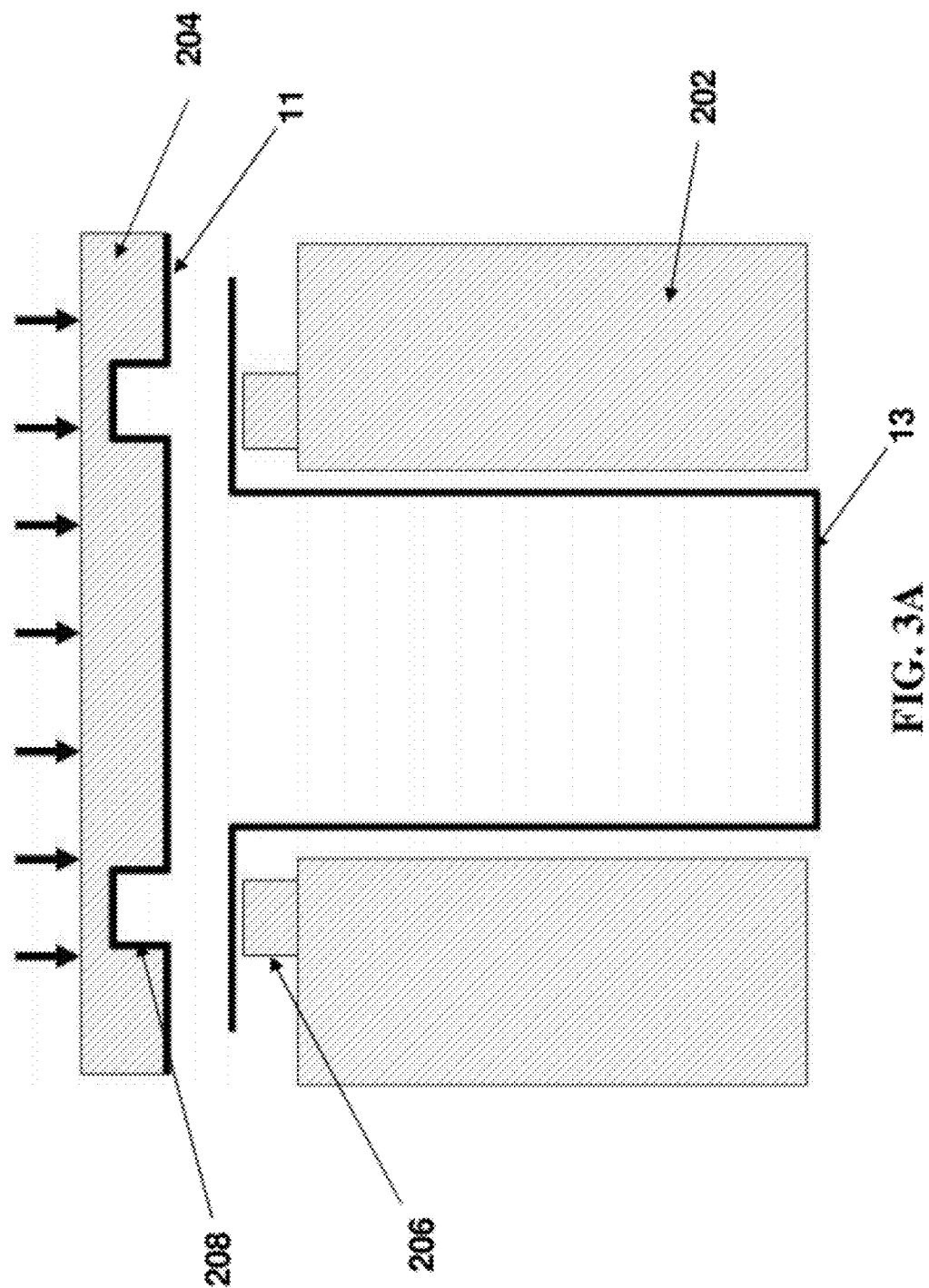

The embodiments discussed herein relate to implantable drug delivery devices (DDDs) that provide one or more low-permeability reservoirs that are also capable of providing a laser-activated release of an active pharmaceutical ingredient (API). To facilitate implantation, the DDD should also have a dimension sufficiently small so as to allow injection into a tissue of the eye.

The low permeability reservoirs described herein facilitate use of sensitive APIs. For example, some treatment regimens require sustained or multiple releases of an API over a long period of time ranging from a week to several months. For APIs that are sensitive to water or air exposure, a low-permeability reservoir protects the API payload and minimizes API degradation over time.

The laser-activated reservoirs described herein facilitate non-invasive release of an API directly to the tissue being treated (e.g., a posterior chamber or vitreous portion of the eye). In addition to being non-invasive, laser activation allows for multiple dosing from a single implanted drug delivery device. Multiple dosing allows the dosing interval to be tailored, providing some control over the drug concentration over time. Laser activation also allows a physician to control the initiation of treatment and administer arbitrary and customized treatment regimens. The selectable nature of the activation and dosing is not realized in existing passive drug delivery device implants.

The individual reservoirs are independent of the formulation and allow the integration of different API forms and types in the overall device. By encapsulating a different API in each reservoir, an optimal formulation for each API can be developed. The overall device therefore can enable multiple drug therapies within one implant. Additionally, when appropriate, multiple API's can be co-formulated within one reservoir.

1. Low-Permeability, Laser-Activated Reservoirs

The embodiments described herein include DDDs that can be implanted into the eye with minimal intervention, are hermetically sealed to protect an API payload over time, and can be laser activated through the retina to selectively release the API as needed. The basic components of embodiments of the DDD described herein include: a reservoir component having an enclosed cavity volume; an API formulation contained in the enclosed cavity volume; and a hermetically-sealed, low-permeability barrier element that maintains the biologic activity or chemical viability of the API until it is intentionally released to the target tissue (such as in the interior of the eye) by laser activation of the DDD. The barrier element may be separate from the reservoir component or may be part of the reservoir component itself. Because the reservoir component is typically formed from two or more parts, the barrier element may also include a low-permeability seal where two or more parts of the reservoir component are joined. Also, as mentioned above, some DDD embodiments have a small diameter dimension that facilitates insertion using a narrow diameter applicator such as a syringe needle.

The materials and design of the reservoir should account for competing constraints with respect to laser activation, hermeticity, implantability, and manufacturability. Some polymers are well suited to thin-wall construction and are compatible with laser activation. For example, some polymers may be easily manufactured as thin-walled reservoirs and may be breached using a pulse of laser radiation. However, these polymers may not provide adequate low-permeability characteristics required for some of the APIs of interest (e.g., biomolecules). Metals, glasses, and ceramics, on the other hand, offer superior barrier characteristics. However, they require higher laser energy to breach and are more difficult to fabricate as thin-wall reservoirs.

The laser activation requires that the barrier layer can be altered or breached by an applied beam of optical radiation. This places additional constraints on the reservoirs. For example, the walls of the reservoirs must be relatively thin (1 to 25 microns), depending on the particular laser mechanism employed (thermal, thermo-mechanical, photo-chemical, photo-disruptive, etc.) If the DDD is to be injected into an ocular cavity, the reservoirs will typically have an internal cavity dimension ranging between 50-500 microns. Larger values are possible if the device will be surgically implanted. Depending on the length of the reservoir, the volume of the enclosed cavity typically ranges between 0.1 to 10 μL per reservoir. The dimension range may be higher for non-ocular applications.

The following exemplary embodiments describe implantable DDDs capable of providing a low-permeability barrier capable of laser activation.

A. Individual Metallic Reservoirs

FIGS. 1a and 1b depict exemplary embodiments of a flanged metallic reservoir before and after sealing. Flanged metallic reservoirs 51 are typically made from two pieces: a cylindrical cup 13 and an end cap 11. The cup 13 and end cap 11 can be joined or sealed to create a shell having an enclosed cavity volume. Typically, the cylindrical cup 13 is filled with an API 20 before the reservoir is closed with the end cap 11.

A complete implantable DDD may include multiple metallic reservoirs contained in a superstructure or tube. In some cases the superstructure is a silicone polymer tube, or a rigid metal structure such as a thin-walled titanium tube. Alternatively, metallic reservoirs may be implanted as a series of separate DDDs, injected or implanted as a depot.

To provide a low-permeability or hermetically-sealed barrier, the cup 13 and end cap 11 may be joined using welding or soldering techniques. For example, a low-temperature soldering process may use a biocompatible solder product material, which contains no silver or lead and can be used in medical grade devices. FIG. 1b depicts metallic reservoir 51 including a hermetic seal 17, which may be formed from weld or solder materials.

Alternatively, the cup 13 and end cap 11 can be joined by applying energy or force to the flange interface 15 between the flanges of the cup 13 and end cap 11. The flared ends or flanges may be produced with very small wall thickness using a deep-draw process such as the process used for the production of precision eyelets by Braxton Manufacturing. The flange configuration depicted in FIG. 1a provides a relatively large surface area at the flange interface 15. A large mating force can be externally applied using a jig or fixture to support the thin flanges of the cup 13 and end cap 15. Examples of techniques to apply the energy to form the bond could include ultrasonic, compression, or resistive welding, as discussed in more detail below.

FIGS. 2 through 4 depict exemplary cold-welded flanged metallic reservoirs. Ultrasonic energy may be added to any of these configurations to increase metal interaction. In FIGS. 2 through 4, cup 13 and end cap 11 components are made from metal foil. Supports 202 and 204 are rigid fixtures, mandrels or jigs used to support the flange portions of the cup 13 and end cap 11. In FIG. 2, supports 202 and 204 with mating protrusion 206 and channel 208, respectively, are used to create shear between flanges of the cup 13 and end cap 11.

The protrusion 206 and channel 208 may be formed using conventional machining techniques such as electric discharge machining (EDM) or may be formed using micro-electromechanical systems (MEMS) technologies such as deep reactive-ion etching (DRIE). The depth of channel 208 should be slightly less than the height of protrusion 206 and the combined thickness of the metal foils used to form the cup 13 and end cap 11. As the mating supports 202 and 204 are first aligned and then urged together, interference of the metal foil and tube flange cause plastic deformation exposing atomically clean metal which spontaneously bonds.

FIG. 3A depicts a similar cold-welding configuration. In FIG. 3A the top support 204 is coated with a metal that is amenable to cold welding (e.g., Au, Ti, Stainless Steel). The metal may be electroplated or vapor deposited onto the top support 204 to achieve the desired thickness. The metal coating the top support 204 is used to form the end cap 11. The embodiment shown in FIG. 3A creates a cold weld due to plastic deformation of the coated metal layer and the flange of the cup 13 as the mating protrusion 206 and channel 208 of the supports (202 and 204) are designed to create an interference fit.

FIG. 3B depicts a similar configuration to FIG. 3A except that an interference fit is created between a step in the top metallized substrate forming the end cap 11 and the cup 13. This configuration has the advantage of allowing thinner device diameter dimension which is an important feature for ocular implants.

FIG. 4 depicts a cross-sectional view of a trapezoidal-shaped top support 204 urging an end cap 11 made from metal foil against the flange of the cup 13. The cup 13 is also a metal foil and is supported by a bottom support 202 with relatively sharp edges such as a machined hole. The edges of the bottom support 202 concentrate the pressure applied to the top support 204 causing plastic deformation of one or both metal foils resulting in a cold weld.

FIG. 5 depicts a similar configuration to the one shown in FIG. 4 except that the top support and metal foil end cap is replaced with a metal plug end cap 11 of a suitable metal material for cold welding. The metal plug end cap 11 may be comprised of a single metal or alloy or may be comprised of a hard underlying metal coated with a soft compliant metal to facilitate cold welding. The compliant metal may be deposited on the metal plug end cap 11 via electroplating or vapor deposition. Alternatively, the underlying material may be a ceramic, silicon, or glass that is metallized.

FIGS. 6A and 6B show supports for flanged cup configurations and fixtures amenable to ultrasonic welding. The ultrasonic welding may be accomplished using a compressive, lateral, or rotational oscillating motion. Both figures show the bottom support 202 as having energy-directing features 210 meant to minimize the contact area between the metal foil of the end cap 11 and the flange of the cup 13 thus maximizing the pressure and interaction between the metals. FIG. 6B depicts an energy-directing feature 210 having a different shape. If the energy directing features 210 are concentric (e.g., having a concentric ring structure), the hermeticity of the seal is improved due to the multiple, concentric hermetic seals. Although not explicitly shown, any of the mating structures shown in FIGS. 2 through 5 could also incorporate energy-directing features to increase metal interaction and shear at the bonding interface. Energy directing features may be on the support or the ultrasonic horn or both. Additionally, the energy directing features are shown distal to the outer diameter of the cup 13 in some of the figures, however, one skilled in the art recognizes that these features may be arranged so that the energy is directed to form the bond at the inner diameter of cup 13 to minimize device size.

Figure 7A:
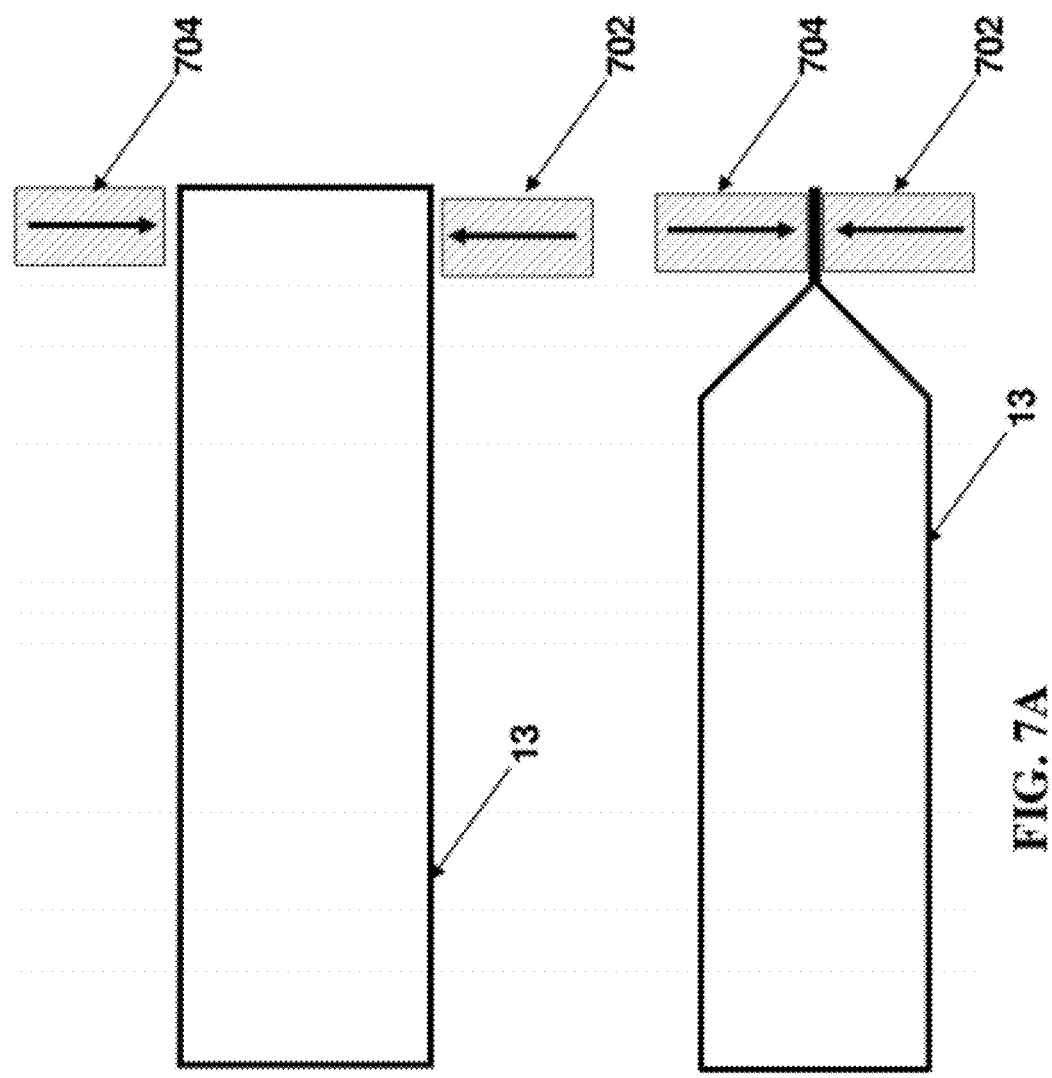
FIG. 7A and 7B depict an exemplary ultrasonic-welded metallic reservoir.

FIG. 7A depicts an alternative configuration in which the reservoir is formed from a single cup 13. As shown in FIG. 7A, the open end of the cup 13 is crimped between a moving support 702 and an ultrasonic horn 704 to form a hermetically-sealed bond. Although not shown, the open end of the cup 13 may also be folded back on itself before being ultrasonically welded in a manner similar to that shown in FIG. 7A.

Figure 7B:
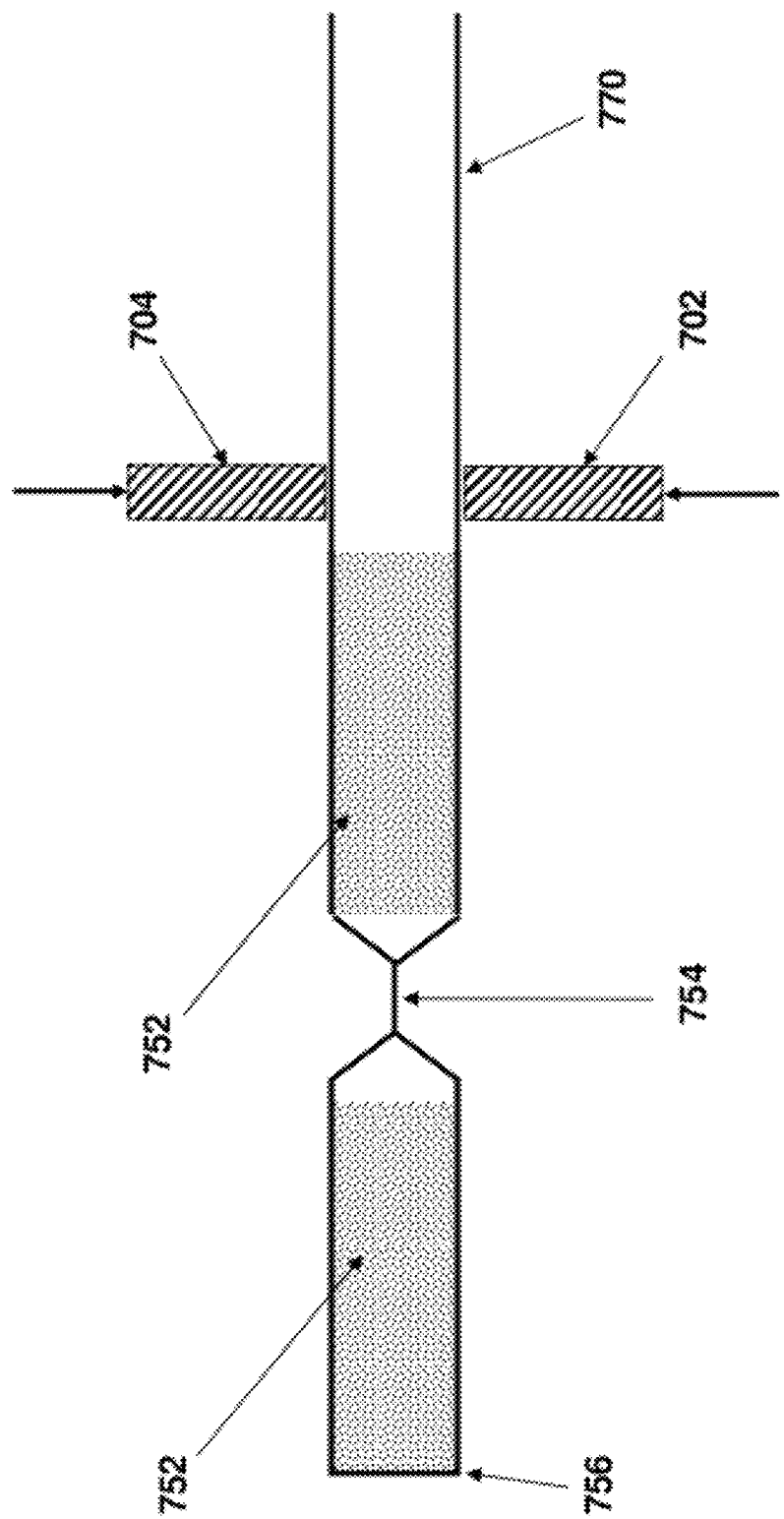

Alternatively, as shown in FIG. 7B, a single tube 770 may be used to construct individual API filled reservoirs during the sealing process. For instance, starting with a tube 770 having a closed end 756, a single API dose 752 may be loaded into the open end of the tube 770 and forced to the distal closed end 756. An ultrasonic bond 754 may be formed at a distance from the closed end 756 to form a reservoir in a similar configuration as shown in FIG. 7A. The process may be repeated, loading the next dose and sealing at a distance from the previous seal to create additional reservoirs.

An alternative seal method may also use a single tube 770, similar to the one described above with respect to FIG. 7B, except that prior to forming the reservoir seal, the tube 770 is twisted to form a constriction adjacent to the previously loaded API 752. The constriction can then be sealed using an ultrasonic pulse or a laser pulse to melt the material in the constriction forming a hermetic seal. The process may be repeated with the next API dose 752 loaded and the tube 700 twisted and sealed until all doses are loaded and sealed.

FIG. 8 depicts a sealing configuration where both supports are comprised of a conductive material and are electrodes for a resistive welding application. In this configuration, a metal foil end cap 11 and flange of a cup 13 are compressed together between a flat bottom support 202 and a top support 204 with energy directing features 210 to increase the local pressure and interaction. Once compressed, a transient pulse of high current passes through the top support 204, metal foil end cap 11, flange of the cup 13, and into the bottom support 202. The high current heats the metal foils at the contact points via Ohmic heat to form a bond.

Figure 9:
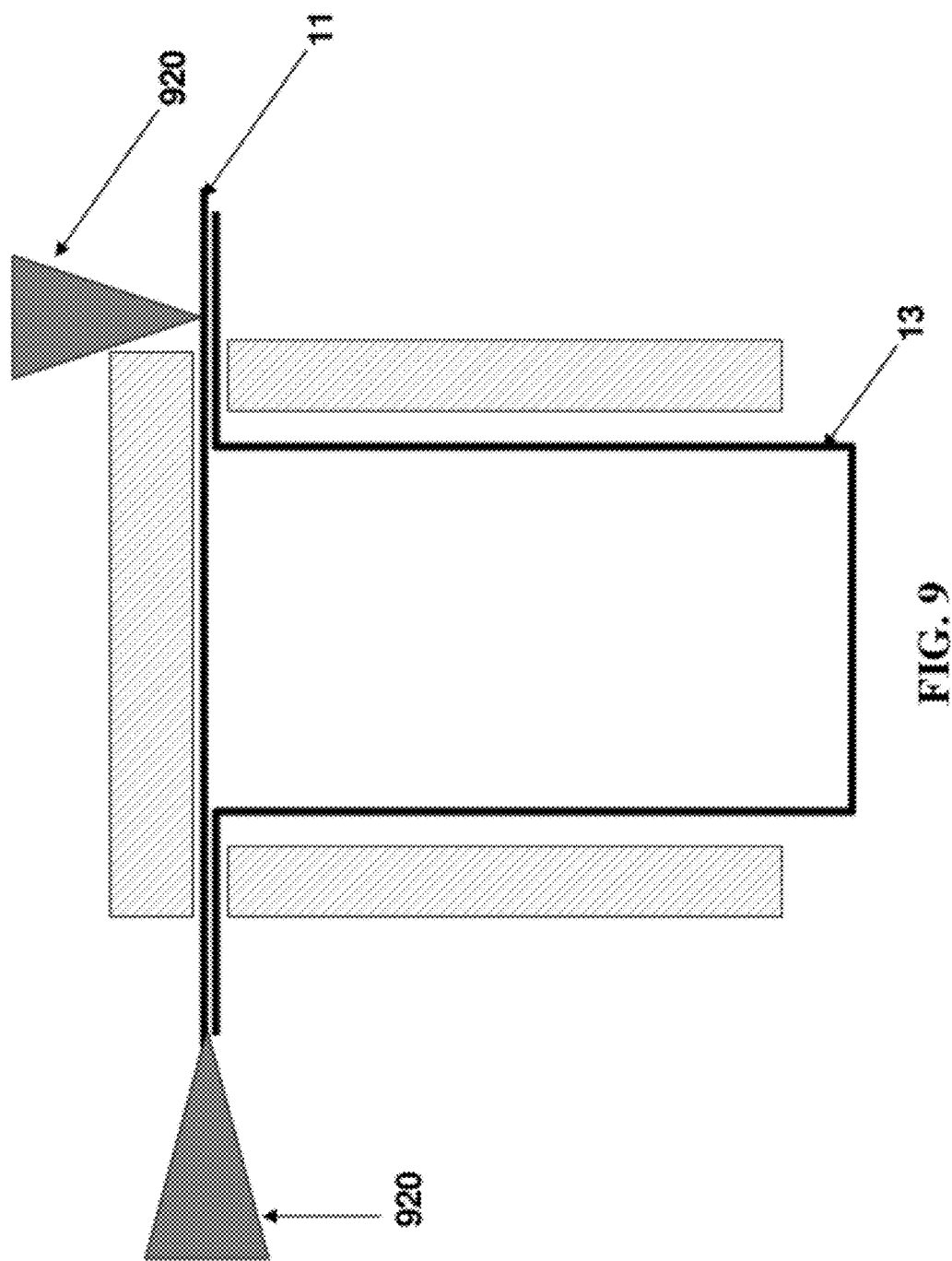
FIG. 9 depicts an exemplary laser sealed flanged metallic reservoir.

FIG. 9 depicts a laser sealing configuration. Supports compress a metal end cap sealing foil 11 against the flange of cup 13. A laser locally heats and melts the metal pair to form a bond. By traversing a pulsed laser beam 920 around the circumference of the tube, individual welds are combined to form a hermetic seal. As shown in FIG. 9, the laser beam 920 may be directed either radially towards the center of the tube or parallel to the tube's axis of symmetry.

Figure 10A:
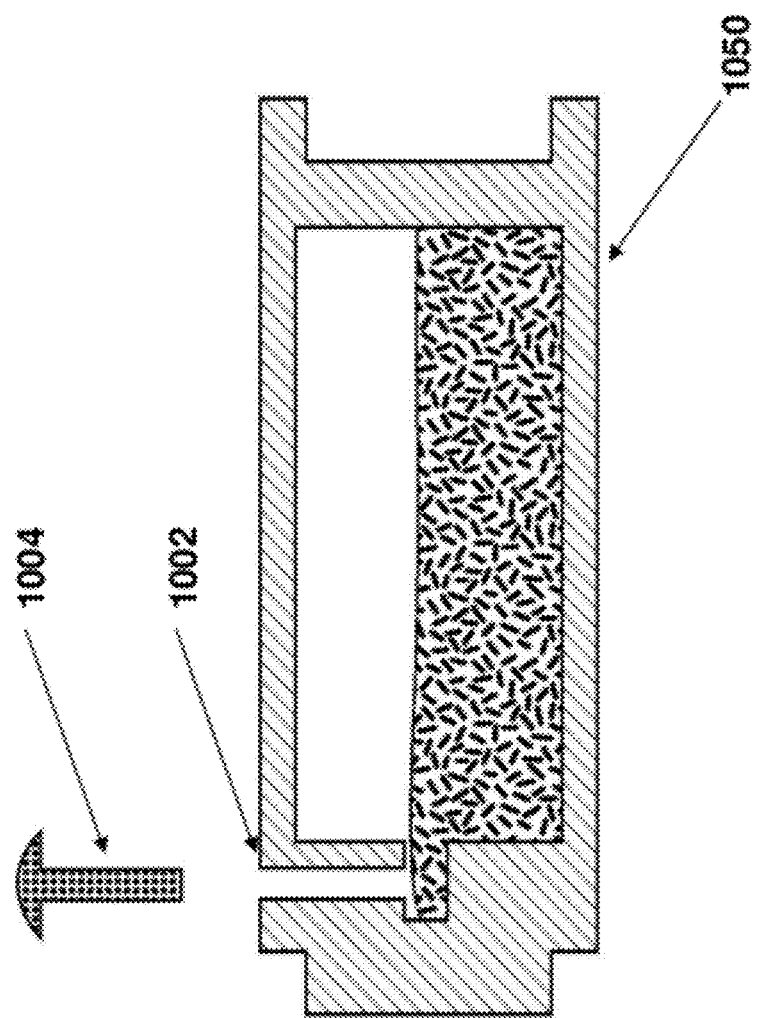
FIG. 10A and 10B depict a reservoir with sealing plug.

FIG. 10A depicts an alternative embodiment of an individually-sealed reservoir. In this embodiment, a nearly completed enclosed metallic reservoir 1050 is initially fabricated with a small opening 1002. The opening 1002 is used to fill the reservoir with an API. After processing the API by lyophilization or other means, a non-hermetic sealing plug 1004 is pressed into the opening 1002. The design of the plug 1004 is such that a metallic coating applied to the top surface of the placed plug 1004 makes a continuous and smooth barrier, which provides the actual hermetic seal. The coating may be metallic, such as gold, Pt, Ti, or other low-permeability, biocompatible coating material.

Figure 10B:
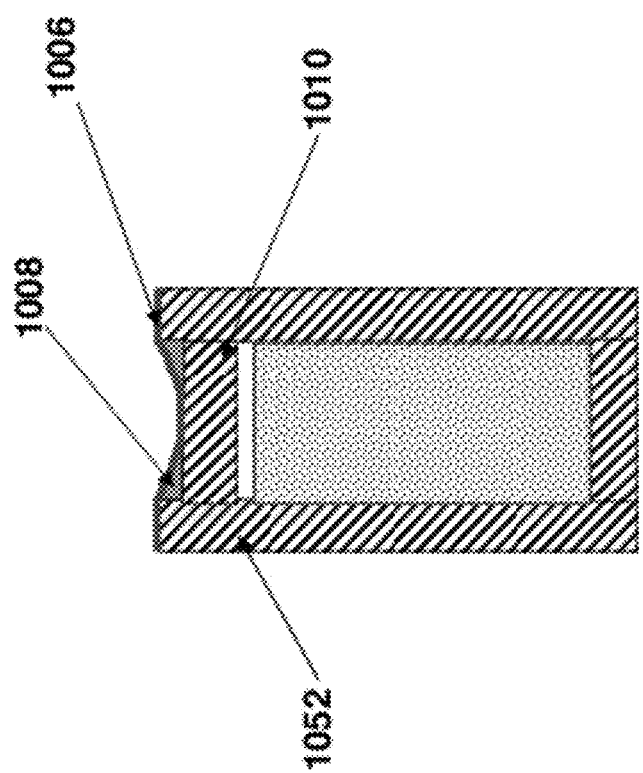

FIG. 10B depicts another alternative embodiment. In this embodiment reservoir 1052 is formed as a cup and can be made from a glass, metal, metal alloy, or ceramic material. The API is added through the open end of the cup. The API may be a solid or dispensed as a liquid and subsequently lyophilized. An impermeable plug 1010 is press fit into the opening of the cup after the API has been loaded. The impermeable plug 1010 may be made from a glass, metal, metal alloy, or ceramic material and is formed to minimize the space between the plug outer diameter and the reservoir inner diameter. With the plug 1010 in place a polymer 1008 is dispensed onto the impermeable plug to seal any gaps that exist between the plug 1010 and reservoir 1052. The polymer 1008 may be a thermoplastic or thermoset and preferably an epoxy or adhesive that bonds to both the plug 1010 and reservoir 1052. A contiguous impermeable coating 1006 is deposited over the reservoir 1052, polymer 1008, and plug 1010 forming a hermetic seal. The coating 1006 may be metallic, such as gold, Pt, Ti, or other low-permeability, biocompatible coating material.

Figure 11:
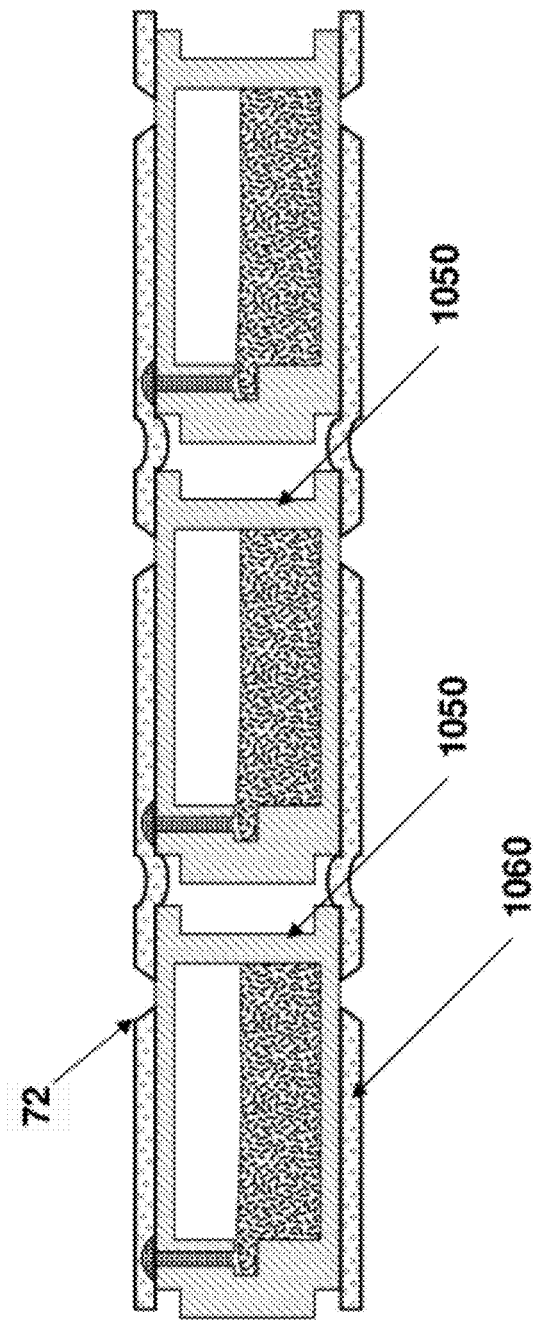
FIG. 11 depicts multiple sealed plug reservoirs in an envelope structure.

As shown in FIG. 11, the individual filled, plugged, and coating-sealed reservoirs 1050 may be placed within a tube or envelope structure 1060 forming a DDD implant with multiple reservoirs 1050. As discussed in more detail below with respect to FIG. 18, envelope structure 1060 may also include holes or other features 72 to allow laser radiation to be directly incident on a portion of a wall of the reservoir 1050.

B. Stacked Metallic Reservoirs

Figure 12:
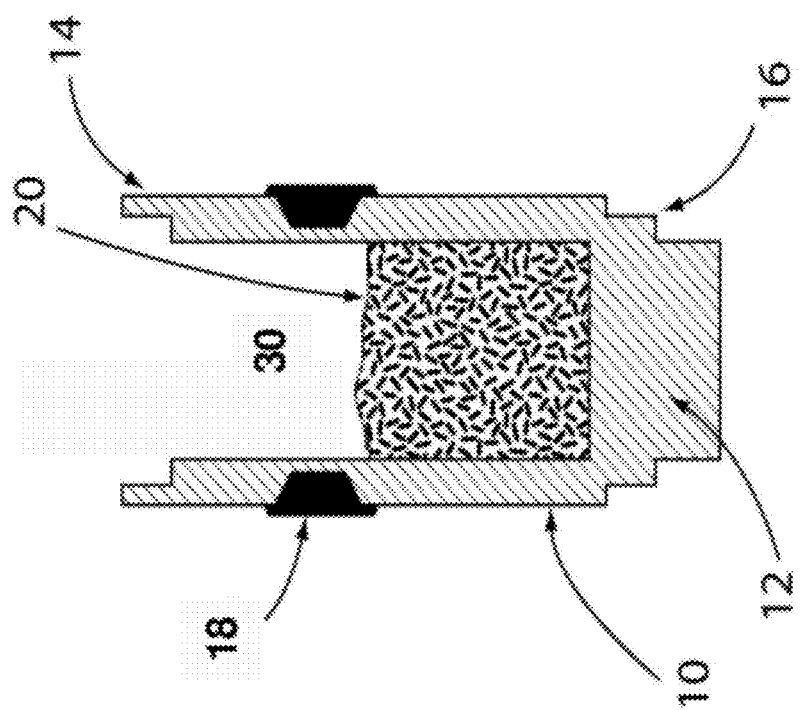
FIG. 12 depicts a reservoir prior to sealing, filled with an API.

Reservoirs can also be made from a single cup or shell having a partially enclosed internal cavity that is open on one end. As shown in FIG. 12, the shell may be shaped so as to allow the reservoirs to be stacked end-to-end. The cavity 30 of the reservoir is at least partially filled with an API 20. As discussed in more detail below, laser-activation sites 18 facilitate laser-initiated breach of the reservoir walls 10, allowing the API to be released from the cavity 30.

FIG. 12 depicts a single reservoir shell made from a metal suitable for hermetic sealing and biocompatible use. The metal is typically gold, but others can be used (Ti, Pt, Nitinol, etc.). The metal is stamped, pressed, or formed into a cup-like shape in advance of the construction of the device. Preferably, the segment is cylindrical in shape, but is in general an open-ended cup or container having a concavity. The outer diameter of the shell is sufficiently small to allow surgical placement or implantation of the completed device into the eye or tissue using an injection technique. Note, the outer diameter of the shell is partially smaller than the completed DDD to allow for the thickness of a tube or envelope structure. Typically, the outer diameter of the shell is less than or equal to 0.5 mm. In cross-section, a shell may have relatively thin walls 10 and a relatively thick or massive bottom 12. The mass or thickness at the bottom 12 allows for proper welding/sealing to a mating shell.

The metallic cross section or thickness of wall 10 may be large enough to maintain mechanical integrity of the shell. Wall thicknesses of the metallic sub-unit are less than 25 μm inch and may be as small as 2 μm. Alternatively, the metallic portion of the shell may be supported by an external layer, such as a polymer film, that provides structural integrity for particularly thin metallic cross-section thicknesses. Thin metallic wall thicknesses may be required in some cases. For example, for low-power laser activation, wall 10 may be less than 10 μm thick.

Shell bottom 12 is relatively thick or massive, which serves several purposes. These include (1) allowing for easier and more robust handling, (2) providing material sufficient to produce metal-metal sealing, and (3) providing a low thermal resistance path for lyophilization of protein or biologics based APIs.

Figure 13:
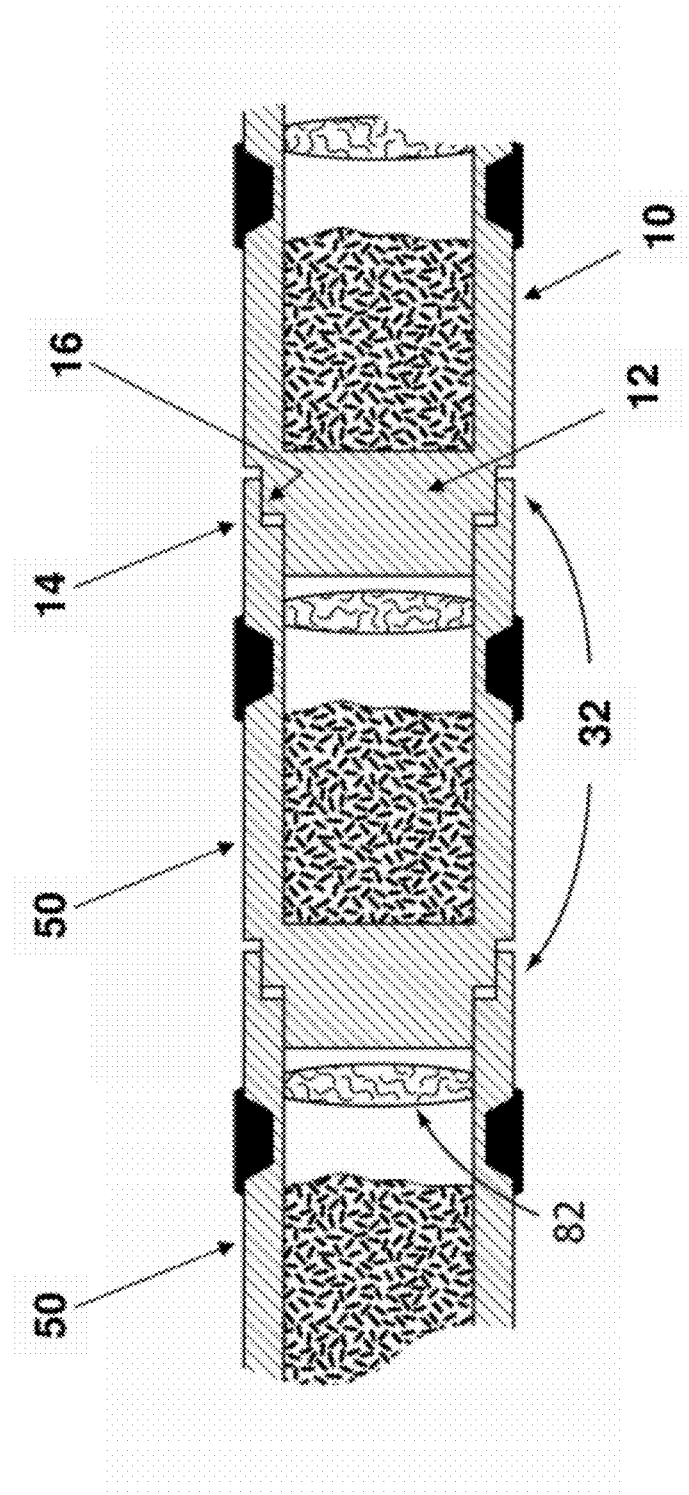
FIG. 13 depicts a drug delivery device with multiple reservoirs stacked end-to-end.

In one embodiment illustrated in FIG. 13, the individual reservoirs 50 are stacked end-to-end. Each shell opening is micro-welded or sealed around the circumference of the base of the next shell. This embodiment minimizes the individual and total length of the weld or sealing contact lines at joint 32.

This configuration reduces potential moisture or oxygen leakage at the bonds. Reservoirs 50 may also contain soluble cap 82 used to protect the API 20, as discussed in more detail below with respect to FIG. 25.

Filled and prepared shells may be aligned using a fixture for assembly and welding. Referring back to FIG. 12, mating features 14 and 16 of shells interconnect in a manner suitable for bonding the metal to make a tightly sealed joint. To simplify fixturing and alignment, the individual welds should be performed by adding one shell at a time. For large production volumes, an appropriate fixture may allow simultaneous or parallel welding of multiple shells. The joint 32, shown in FIG. 13, may be cold welded by a mechanical impulse, or by a slower mechanical pressing. Alternatively, applied localized energy in the form of a spot arc welder, an ultrasonic welder, a laser welder, or a radio-frequency welder may be used to produce a metal-metal seal or joint. Suitable welding technologies must be employed on a small scale, as the size of the joints 32 may be as small as 25 μm across (and extending circumferentially around the joining of two adjacent segments.) The shell bottom 12 (see FIG. 12) may be relatively massive, with sufficient metal material present to allow for robust welding or joining between shells. Conversely micro-welding may be used to produce the joints, requiring the open end mating feature 14 (see FIG. 12) to be thin and low mass reducing the heat energy required to produce the seal. A thickness of 25 μm or lower is desirable.

Alternatively, shell bottom 12 may be comprised of a material that is different from the shell walls 10 and shell mating feature 14. Shell bottom 12 may be comprised of a harder metal or material to provide a rigid underlying support. By urging two stackable shells together under sufficient force, mating features 14 and 16 may flow, improving the metal-metal bond. Alternatively, shell bottom 12 may be comprised of more than one material; a hard underlying core coated with a thin (e.g., electroplated gold) soft material. The open end of the final shell segment may be capped with an appropriately formed end piece that lacks a cavity.

Multiple reservoir embodiments may also be capable of delivering multiple doses from a single activation event of a compound reservoir or from reservoirs having internal (non-hermetic) communication channels or pathways. This is desirable when drug dosing is required to be pulsatile in nature, or when the number of laser interventions is required to be lower than the number of individual dosing events, or when the duration of treatment associated with a reservoir and a laser activation exceeds the characteristic time of bioavailability of the particular API. For example, a protein such as bevacizumab may have a half-life in the eye of approximately 9 days. If the desired period of a treatment from a reservoir is 90 days, the concentration at day 90 is only approximately 0.1% of the concentration at day 1. Thus, even relatively large amounts of API loaded into a reservoir may not be efficacious over the entire 90-day period. As an alternative, a staged release of two or more individual sub-doses may provide the appropriate drug concentration profile over the treatment period.

Figure 14:
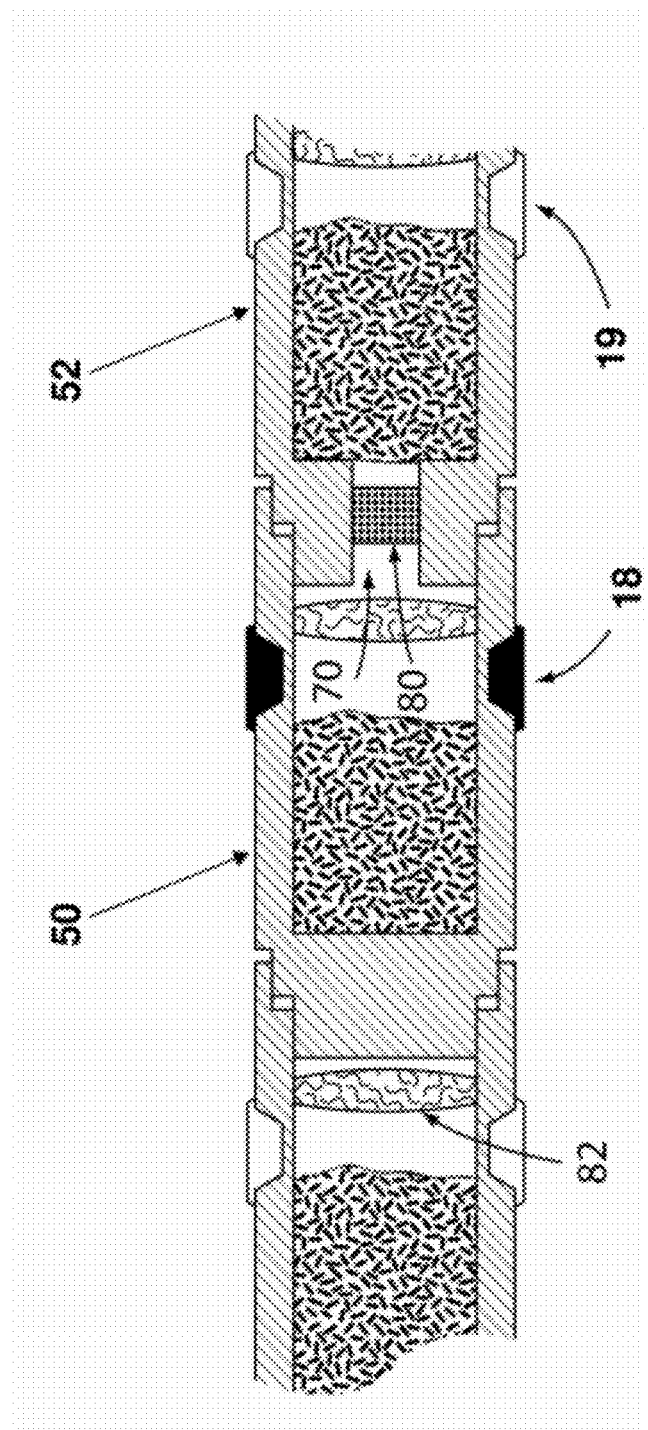
FIG. 14 depicts a drug delivery device with multiple reservoirs stacked end-to-end and a channel pathway.

For example, as shown in FIG. 14, single opening reservoirs shell segments 50 can be combined with reservoir segments 52 with additional openings or channel 70 in the base. The additional opening can be used as a fluid path between the enclosed cavities of adjacent shell segments. An erodible polymer membrane or block 80 may be placed into the opening, by polymerization, flowing, or molding. Block 80 may also be mechanically placed into channel 70 using an interference-fit between the block 80 and channel 70 to create a tight, but non-hermetic seal.

In some embodiments, the DDD is constructed alternating solid-base shell segments 50 and open-base shell segments 52 placed in the assembly fixture. The mating features 14 and 16 may be welded and sealed as explained above with respect to FIG. 13. The DDD shown in FIG. 14 is similar to FIG. 13, with the addition of a channel 70 and passive barrier 80, which allows for time-delayed multiple doses from a single laser activation.

In one embodiment, the polymer chosen for the passive barrier 80 may be of the class of polyanhydrides or other polymers that are relatively hydrophobic which over time degrade by a surface erosion mechanism to give a pre-determined time at which the seal will transition from fully blocking to open, providing for a definite time period to release.

In another embodiment, hydrophilic "bulk-eroding" polymers that are more permeable or soluble may be employed, with a faster, or immediate and continuous, release of the API in the second segment. These barriers will not provide for a time period of sealing after initial exposure of the passive barrier to fluid, water or other agents, which erodes the passive barrier.

In another embodiment, mixing these classes of materials, or co-polymerizing them, may be used to create custom and complex release profiles of API release. A first release from a segment 50 may be accompanied by a second, distinct, but temporarily overlapping release from segment 52, to give complex release profiles of one or more APIs, but may also be initiated at a user-determined activation time.

In the embodiments described above, the polymer barrier does not contain a drug, but the material may utilize the similar polymers used in the creation of microsphere drug formulations. The delayed-release polymer barrier may be made from poly (L-lactic acid), poly (lactic-co-glycolic acid), ε-caprolactone, ε-caprolactone-co-ethylene oxide, polyacrylate, cellulose acetate, polyurethane, polystyrene, poly (orthoester), poly(hydroxybutyrates), polyethylene glycol (PEG), polyethylene oxide (PEO), polyvinyl pyrrolidone (PVP), ethylenevinyl acetate (EVA), polyvinyl alcohol (PVA),silicon polymers or combinations/mixtures of the above. It should be understood that the polymer(s) thickness, porosity, and composition may be used independently or in combination to design a delayed or modified release profile. The polymer barrier may be a contiguous film, filaments, lattice, or a mesh.

With reference to FIG. 14, shell segments containing passive barriers may be fabricated with non-laser absorbing material at site 19 such that laser energy directed at site 19 will not cause absorption and subsequent laser activation. Contrast with the laser-activation site 18, which is an area of the shell wall that can be perforated or breached using laser irradiation and allow elution of API into tissue. This configuration may be desirable if the order of cavity activation is important or may prevent inadvertent activation of an already emptied segment or drug reservoir. Laser activation is discussed in more detail below.

As shown in FIGS. 14, 13, and 11, individual reservoirs can be combined to form a single DDD. The small diameter of the reservoirs allows the construction of a low-profile, implantable DDD. In some cases, connected reservoirs (using welding or bonding) are sufficiently strong to form the complete DDD implant. Alternatively, the entire assembly of reservoirs may be inserted into a polymer tube or envelope structure to protect and support the DDD implant. The assembled reservoirs may also be coated with a polymer or other material to protect the reservoir walls and seals from mechanical forces associated with handling and implantation. Such polymers or coatings themselves may be bioerodible or biodegradable such that after implantation and deployment, the protective superstructure erodes away leaving the hermetically-sealed structure.

C. Ampule Reservoirs

An alternative series of embodiments employs glass, ceramic, insulator, semiconductor or dielectric microtubes to create sealed reservoirs in which the ends are sealed with metallic caps to enable the fabrication of a multi-reservoir DDD. These embodiments may be referred to as micro-ampules or ampule reservoirs.

Figures 15A, 15B:
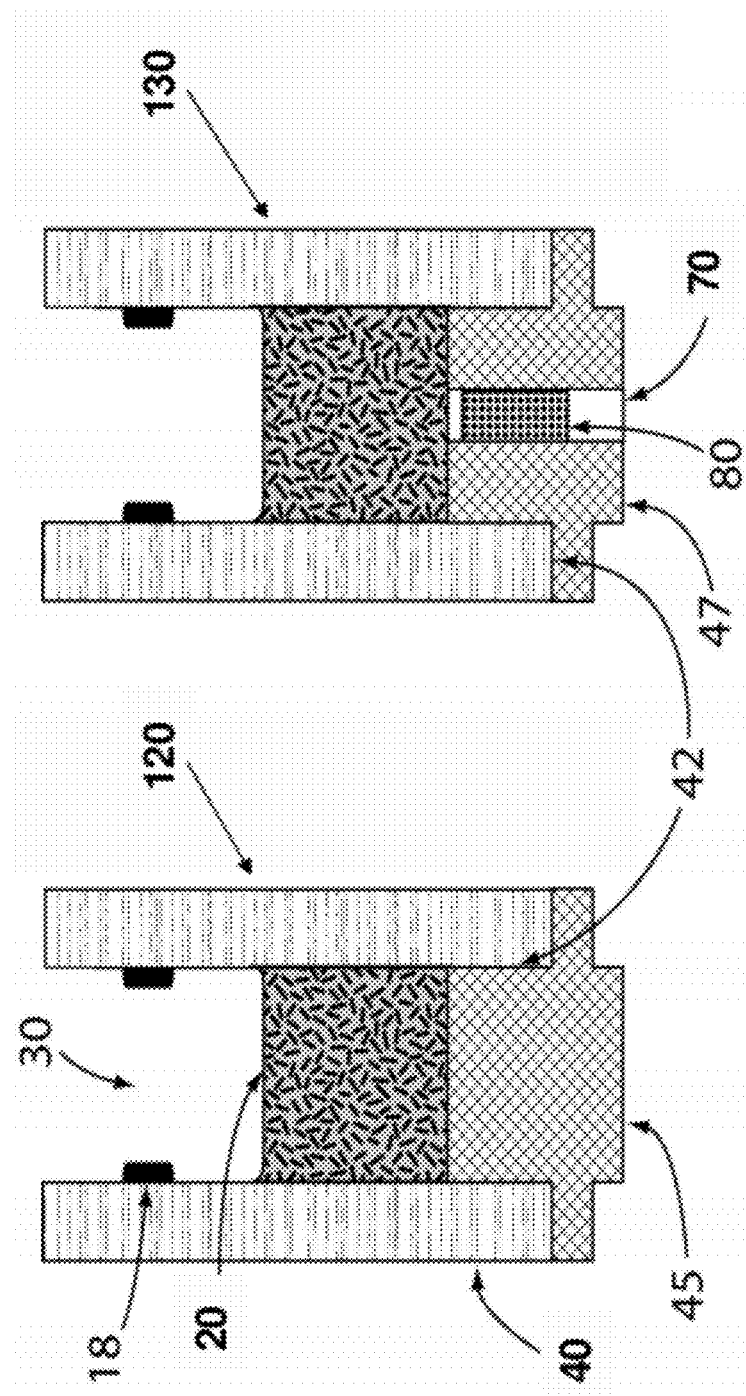
FIGS. 15A and 15B depict ampule reservoirs.

FIG. 15A depicts single micro-ampule reservoir 120 comprised of a thin-walled glass tube 40 capped at one end by metal base 45, which may consist of metallic coatings, plugs, or caps. Metal cap 45 is shaped so that the bottom or external portion of the cap can be inserted into the open end of another glass tube. This configuration allows the ampules to be stacked end-to-end.

FIG. 15B depicts single micro-ampule reservoir 130 comprised of a thin-walled glass tube 40 capped at one end by metal base 47, which may also consist of metallic coatings, plugs, or caps. Metal cap 47 is also shaped so that the bottom or external portion of the cap can be inserted into the open end of another glass tube allowing end-to-end stacking. Metal cap 47 also includes channel 70 and dissolving plug 80 that can be used to disperse the contained API 20 into the cavity 30 of a mating ampule reservoir. These features are discussed in more detail below with respect to FIG. 18.

With regard to FIGS. 15A and 15B other materials can be selected for tube 40, including other types of insulators, dielectrics, ceramic materials. The selected tube material should be highly impermeable and should be relatively brittle or fragile. Examples of these materials include semi-crystalline quartz, photo-lithographically constructed semiconductor structures, fused silica, Apex photodefinable glass, etc.

Thin-walled microcapillary glass tubes may be used as the base material. An example is the standard product available from PolyMicro, Inc, part number TSP320450. This tube is a fused silica capillary of outer diameter 450 microns and inner diameter 320 microns, which corresponds to a glass wall thickness of 65 microns. Thinner walls are desirable, such as walls as thin as 25 microns, but fabrication techniques for extremely thin glass walls limit how thin they can be.

Gold caps or bases having a T-shaped cross section and axially symmetric shape, are mated to the ends of the glass capillary, which may be pre-coated with a thin layer 42 of gold, titanium, or other metal or coating material typically used to create an adherent layer for glass-metal sealing. Other metals such as Ti, Pt, etc., may also be used. Glass-metal seals of this type can be used in high vacuum applications in which pressures as low as $10^{-10}$ Torr are maintained, making this seal type an excellent choice for the creation of a hermetic seal.

The end caps or bases may be inserted and soldered, pressed or welded onto the pre-coated ends and interior and exterior surfaces of a glass capillary. Alternatively, the tube may be inserted into a larger diameter end piece fabricated from metal, as in U.S. Pat. No. 4,509,880. In this embodiment, an interference fit is formed between a larger inner diameter metal end cap or base and a smaller outer diameter glass tube, with the joint made hermetic by flowing of solder.

API 20 is loaded into the ampule with the thicker metallic (typically gold) end cap base in place, with a (possibly thinner) top end cap 46 sealed after the API has been loaded in cavity 30. (See FIG. 16.) Top end cap 46 may alternatively be a metal foil that is ultrasonically bonded to the metallized glass surface. Laser-activation site 18 is an area of the glass capillary that, when irradiated with a laser, fractures, perforates, damages or otherwise causes the integrity of the glass tube walls to fail and allow elution of API 20 into tissue. Properties of a laser-activation site 18 are discussed in more detail below.

Figure 16:
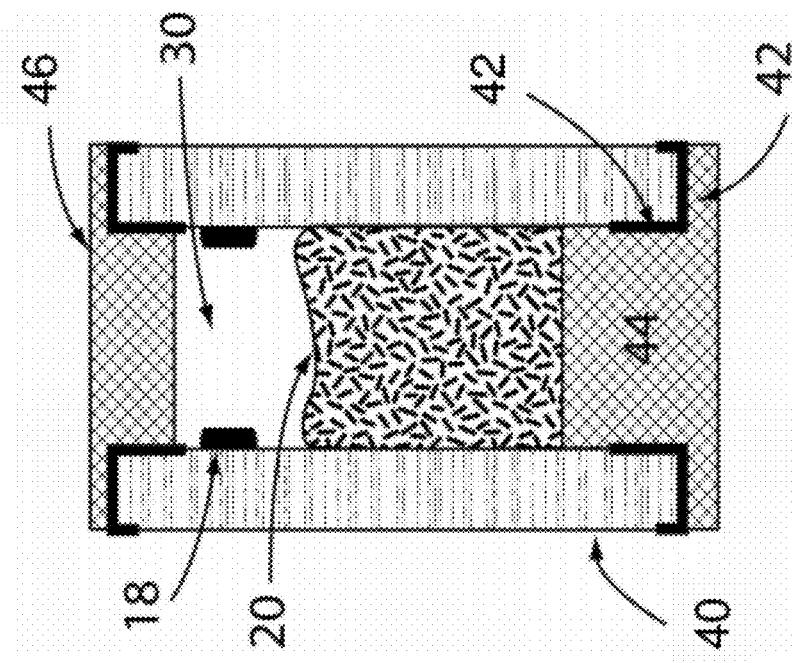
FIG. 16 depicts a filled and sealed ampule reservoir.

FIG. 16 depicts an ampule with solid metal end cap 46 and base 44 which may be sealed to the metalized glass by cold-welding under pressure or mechanical impulse, or may be sealed through the application of a micro-welding energy pulse to or near interface 42 from an electrical arc welder, an ultrasonic welder, a radio-frequency welder, or a laser spot welder. The intrinsic low thermal conductivity of the glass allows for a relatively strong applied welding pulse energy without risking thermal damage to the API payload 20.

In another alternative sealing approach, a low temperature soldering process may be used, for example with the biocompatible product: EWI's SonicSolder, which contains no silver or lead, and is used in medical grade devices.

In cross-section, the glass capillary tube 40 may have relatively thin walls to minimize the device size for implantation, but also importantly to allow for minimal laser energy requirement to perforate, damage, or otherwise open the glass wall. One or both metallic end cap 46 and base 44 may be relatively thick or massive. The mass or thickness of the segment end or bottom allows for sufficient material to provide proper glass-metal sealing. Additionally, the low thermal resistance of a relatively massive metal end cap or base is useful in the lyophilization process that sensitive biologic APIs may require.

Figure 18:
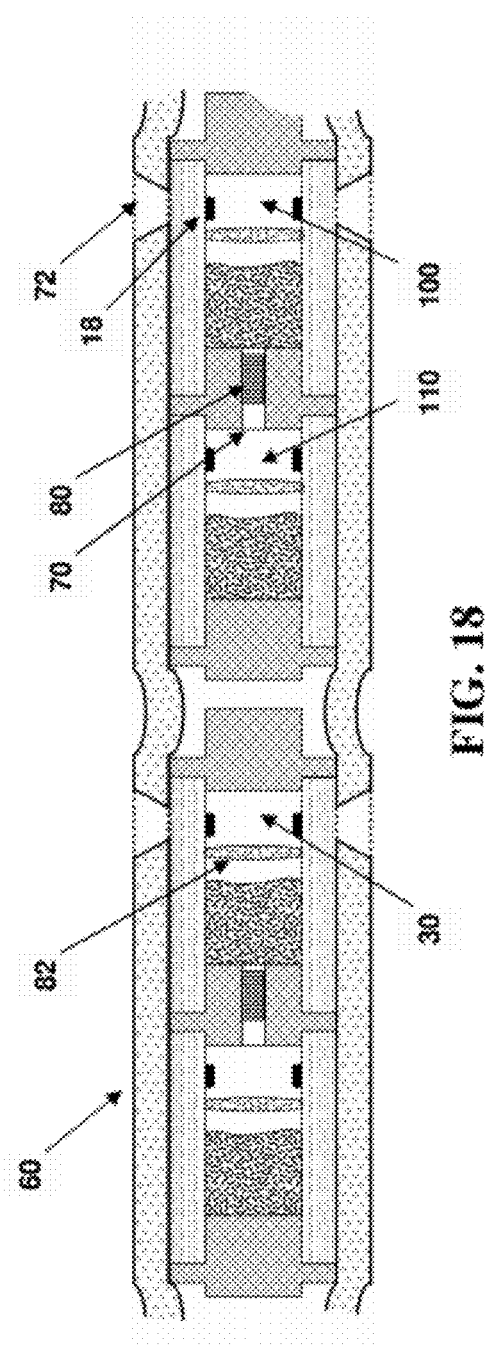
FIG. 18 depicts multiple ampule reservoirs in an envelope structure with channels between ampule reservoirs.

A further embodiment of the present disclosure is a hermetically-sealed multiple release micro-ampule structure. As shown in FIGS. 15A and 15B, micro-ampules 120 are constructed using solid bases 45, and micro-ampules 130 are constructed using bases 47 that have an opening or channel 70. A multiple release micro-ampule DDD assembly is depicted in FIG. 18. The channels 70 of bases 47 are non-hermetically sealed with an erodible polymer membrane or block 80 that is placed into the glass capillary, by polymerizing, flowing, or interference-fitting the polymer to create a tight, but non-hermetic seal. The polymer chosen for this passive barrier may be either of two classes, (1) bulk erosion polymers or (2) surface erosion polymers. Both classes of polymer degrade by hydrolysis, but the mechanism is different. Bulk eroding polymers may be engineered as co-polymer or by other means to enable degradation over a prescribed time while preventing water or gas from penetrating the material, though the intrisinic degradation mechanism is bulk rather than surface. An example of this class is the PLA/PLG/PLGA (poly lactic acid/poly glycolic acid/copoly lactic acid/glycolic acid). Surface eroding polymers degrade by intrinsic hydrolysis of the surface layers without engineering of their microstructure. An example of this class is the polyanhydrides. Those knowledgeable in the art may easily design such eroding seals with arbitrary release times from hours to months in length.

As shown in FIG. 18, the micro-ampule reservoirs may be (potentially aseptically) loaded with API and may be lyophilized or otherwise processed to stabilize the API, and may include protective caps 82 inside the ampule cavities 30. The bases 47 of reservoirs 130 may then be hermetically sealed in a glass-metal seal to reservoirs 120, and the end of reservoir 130 may be sealed with a second base 45 to form two-chambered hermetically-sealed micro-ampules. This approach may be extended to an arbitrarily large number of chambers, with the limit on the number determined by the mechanical fragility of the assembly and the practical limit on the length of the resulting implant device.

As in other embodiments, multi-chambered micro-ampules may be placed inside in a polymer tube or other envelope structure, such as a heat-shrink polyolefin tube, or a solvent-shrunk silicone tube to create a long, thin DDD implant. For exemplary embodiments, see FIGS. 17 and 18.

As shown in FIG. 18, the ampules can be assembled so that multiple doses may be released from a multi-chambered micro-ampule in a DDD using a single laser activation event. Laser activation at location 18 exposes the first chamber 100 to fluid or other biological substances. Fluid entering first chamber 100 causes API to elute through an opening created at site 18, providing an initial dose of drug to tissue. The side of the passive barrier 80 exposed to the fluid in chamber 100 erodes over a prescribed time. After the passive barrier 80 has been eroded, biological fluid begins to enter the second chamber 110 of the adjoining ampule reservoir via channel 70, causing the API in the adjoining reservoir to elute into second chamber 110, first chamber 100, and subsequently through the laser-activation site 18 and into tissue.

Figure 17:
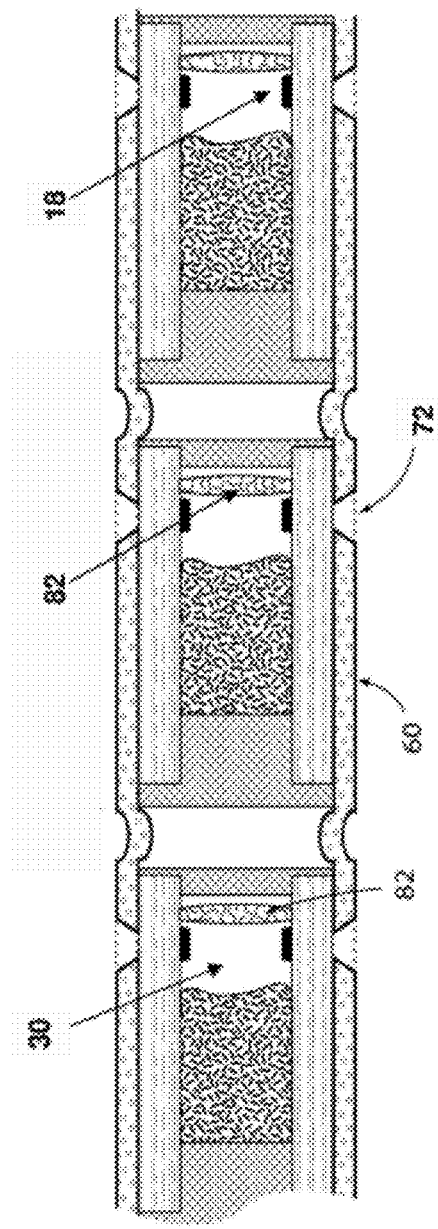
FIG. 17 depicts multiple ampule reservoirs in an envelope structure.

Referring to FIG. 17, individual micro-ampules are placed in a fixture, end-to-end. The linear arrangement is then inserted into a sleeve 60 that acts as a superstructure to hold the assembled ampules together, in a thin, long cylindrical DDD. Such a cylindrical arrangement allows for implantation with a minimally-invasive needle or other applicator, is simple to assemble, and allows for a significant numbers of doses/ampules to be included in a single, easily-identifiable and locatable device. Incorporated by reference is patent application Ser. No. 12/910,572 "Providing a Visual Indication of Rupture or a Drug Reservoir Implanted within an Eye," filed Oct. 22, 2010, in which various methods are described for visually indicating the individual reservoirs, their particular status (empty, full, API type), a location for laser targeting, and a means of determining visually the success or failure of a particular laser activation attempt to activate or release the contents of a reservoir.

A permeable tube, such as a molded or extruded thin wall silicone tube may be used for sleeve 60. Alternatively, a polymer or other material that is not particularly intrinsically permeable, but is perforated, meshed, or otherwise contains openings that allow ingress of fluid and egress of eluting drug substance may be used. If the material is continuous as in the silicone tubing example, the optical properties of the material must allow for significant transmission of the applied laser beam.

If a silicone tube is used for sleeve 60, the complete DDD may be fabricated using solvent swelling to temporarily expand the tube (by soaking in an appropriate solvent before assembly), allowing the expanded silicone tube to be placed over the linear series of ampules, and subsequently dried to shrink the tube onto the ampules.

Non-optically-transparent polymer shrink tubing may also be used as sleeve 60, providing a simple means of assembly. An example of such a material is the ePTFE medical grade shrink tubing from Parker Hannifin, TEXPORE™. This material can be heat shrunk onto the linear arrangement of micro-ampules, and will allow ingress of fluid (water) and elution of drugs, or even relatively large particles. In this example, holes or other features 72 must be pre-formed in the shrink tube 60 to allow access of the laser radiation to the activation sites 18.

In the embodiment in which a permeable tube is used, such as a transparent silicone tube, fluid and drug substances are able to cross the polymer barrier and laser light can transmit through the tubing wall. In the case of silicone, however, shrink tube based assembly cannot be used, and extrusion or other methods for enveloping the micro-ampules inside the tube may be used. This embodiment has the additional advantage of completely containing in the structure any glass particles that fragment from the laser damage of the glass wall, preventing small amounts of glass from reaching tissue.

Alternatively, "bare" micro-ampules may be injected or implanted serially to form a collection of individual devices. They may be injected into the eye and allowed to be located in a dispersed manner, or they may be placed into a previously-deployed receptacle, such as a polymer bag, a gel depot, or a rigid mechanical form, such as a previously implanted sleeve.

D. Metal-Clad Polymer Reservoirs

Another embodiment of an implantable, laser-activated DDD uses metal-clad polymer reservoirs. In general, thin layers of gold or other noble or refractory metal make effective barriers. It is desirable to have the barrier layers be very thin (<25 µm thick, and preferably <3 µm thick) such that a pulse of laser radiation can cause a breach or alteration in the barrier. Such thin layers must typically be supported by some material. Moderately thin sheets of polymer may be coated with such metals and used to construct the DDD.

One variation uses sheets of a flexible polymer film coated with a metal layer to construct an API reservoir substrate that can be laser activated. The polymer film may be, for example, polyethylene or another polyolefin that can be easily doped with a laser absorbing material, and can be easily locally melted or ablated by an applied laser beam. The metal layer, most ideally gold, is constructed by physical deposition or some other coating technology, that allows for a contiguous, highly impermeable and inert layer. Typically, the metal layer will be at least 1 micron thick. The polymer film or other layer that the metal is bonded to is the agent and initiation site of the laser perforation. The optical radiation from a laser beam is absorbed and a thermo-mechanical (or other laser interaction) acts upon the polymer film, which may be considerably thicker than the metal layer. An example is a low-melting-temperature polyolefin polymer, such as high density polyethylene (HDPE) doped with highly absorbing black carbon material. The laser energy, heavily absorbed by this material, easily melts the relatively bulky polymer film and removes with the melt zone, the relatively thin metal layer (e.g., gold), allowing the API to elute.

Figure 19:
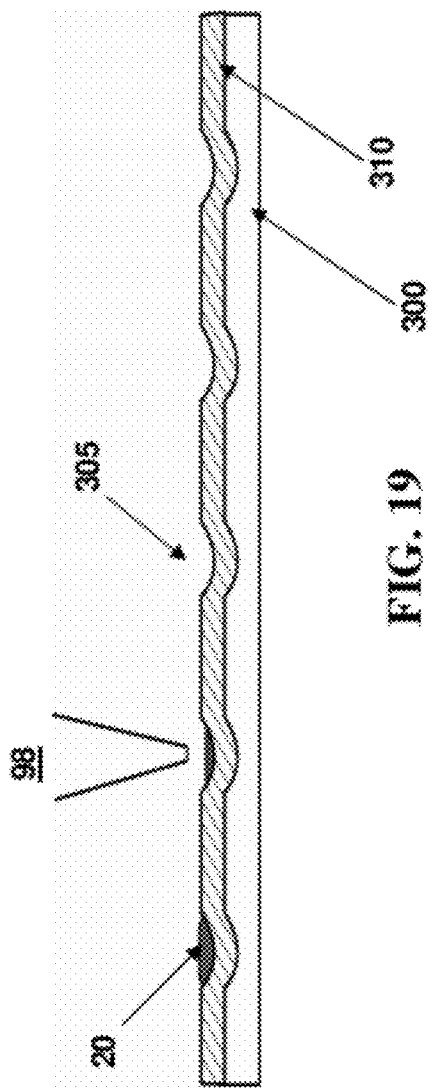
FIG. 19 depicts a polymer-metal laminate reservoir structure with an API dispensed into individual well features.

Referring to FIG. 19, a thin coating of gold 310 on one side of a first polymer sheet 300 is used to place one or more solid formulated or liquid dispensed API doses 20. Wells 305 or other features may be preformed in the gold-coated polymer sheet 300 to localize and contain the dispensed API doses 20. FIG. 19 also depicts exemplary dispensing nozzle 98. For many APIs, lyophilization of the formulation may be required after dispensing.

The metal layer 310 faces the formulated API 20. A second, similarly coated polymer sheet is then placed over the solid formulated disks or pellets, with the metal layer facing towards the API, and towards the opposing metal surface of the first sheet. This assembly may be placed onto a hard molding surface, such as a steel plate. An opposing hard surface (plate) then squeezes the layered assembly together, preferably with a high pressure impact, but may be accomplished by stamping or other mechanical means. The applied force is sufficient to cold-weld the metal surfaces of the sheet subassemblies together. An advantageous embodiment uses features in the sheets which have at least a partial orientation out of the plane of the sheet to facilitate the loading of normal or perpendicular stress applied to the sheets in order to cause the metal coating to flow and cold weld.

Figure 20:
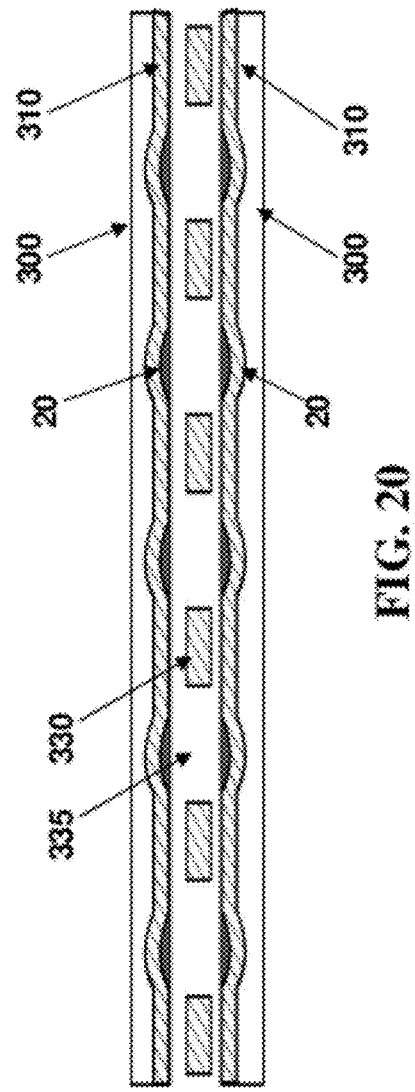
FIG. 20 depicts a polymer-metal laminate reservoir structure loaded with an API, prior to sealing.

The amount of metal material in the two coating layers may not in some cases be sufficient to make a good cold-weld seal. As shown in FIG. 20, a thicker metal mesh 330 can be inserted between the metal-coated polymer film to supply enough metal to flow and establish a seal, while still leaving most of the barrier a thin layer. The mesh 330 is structured to have wells or holes 335 where the solid formulation shapes are to be located. Two subassemblies are bonded by cold-welding to a mesh, grid, or sheet of metal. In some cases, the mesh, grid, or sheet of metal is gold.

Figure 21:
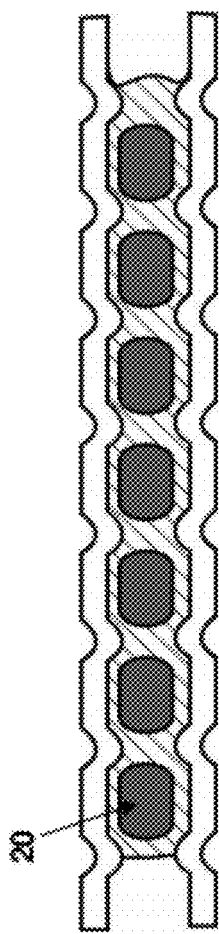
FIG. 21 depicts a polymer-metal laminate reservoir structure loaded with an API, after sealing.

FIG. 21 depicts a cold-welded, hermetically-sealed composite structure containing multiple reservoirs filled with an API 20. The reservoirs can be cut into individual sealed reservoir elements that are suitable for insertion into a narrow profile carrier, such as a tube, or may be used directly as free-floating assemblies, each sealed, and each implanted into the eye tissue. Alternatively, the assembly may be fabricated to form a linear device that can be used as the actual implant, or may be further processed by inserting the sealed assembly into a carrier structure, such as a thin, optically transparent tube of polymer. The envelope structure (tube, sheet, etc.) should allow for laser beam access (transparency), and must allow the elution from a laser-activated device to proceed. This second requirement allows for a variety of designs, including a drug/fluid permeable material choices such as EVA for the tube, or the tube itself may erode or dissolve away after implantation (such as, for example, a PVA film). Or the material may have a mesh or perforated structure, allowing for many sites for fluid and drug transport.

Figure 22B:
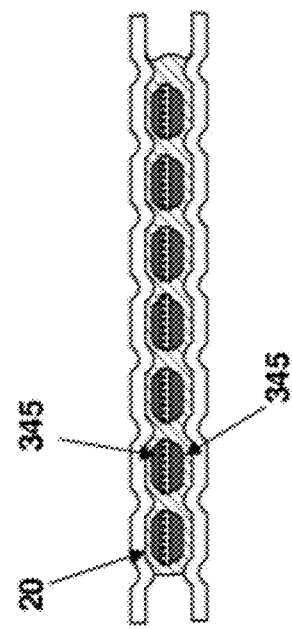
FIGS. 22A and 22B depict a polymer-metal laminate reservoir structure with an erodible barrier between API cakes in a multi-chamber reservoir, prior to sealing and after sealing.
Figure 22A:
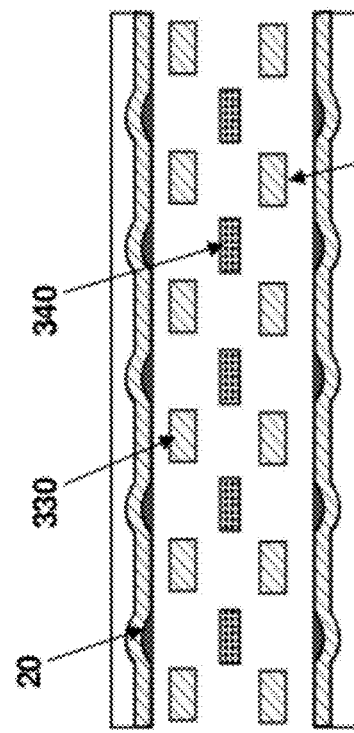

Additionally, as shown in FIGS. 22A and 22B, multiple metal mesh layers 330 may be used with an erodible polymer sheet 340 to create two or more separate chambers 345 within a single hermetically-sealed reservoir. As in the example above, two subassemblies carrying dried (lyo-ed) API "cakes" are bonded to form an assembly by cold-welding. In this embodiment, two separate meshes, grids, or sheets of metal (e.g., metal sheet 330) are formed by stamping or other mechanical means, trapping another layer of erodible, soluble or biodegradable material, such as a polymer film of PVA or PLGA. (e.g., erodible polymer sheet 340)

The resulting composite structure has individual reservoirs completely hermetically sealed by metal (gold) with other, non-hermetic structure. Outer structure can supply form, strength, and laser absorption character, while allowing the thin hermetic layer to perform sealing. The thickness of the metal layer is such that thermo-mechanical damage to the polymer structure removes, breaches, or otherwise penetrates the hermetic layer.

FIG. 23 depicts a cross-section view of an individual reservoir with two hemispheres representing two separate API doses (22 and 24) in a multi-chambered (345) embodiment of a cold-welded polymer-metal laminate reservoir. The result is a divided reservoir with a first API dose 22 eluting from a chamber 345, which has been breached using laser beam 350. The symmetry of the device allows a chamber 345 on either side to be activated with laser beam 350. Laser perforation occurs when thermo-mechanical destruction of the polymer structure removes the thin but hermetic metal layer. A second API dose 24 elutes when the passive barrier 360 formed by the divider becomes permeable or erodes away during exposure to fluid. FIGS. 21, 22A, 22B, and 23 are merely exemplary and other geometries are possible.

E. Hermetically Coated Reservoirs

Other classes of materials beside metals may be deposited to create an impermeable layer onto polymer substrates. For example, Barix barrier film from Vitex Systems Incorporated consists of alternating layers of silicon dioxide and polymer to form a hermetic laminate structure. See, U.S. Pubs. 2007/0196682 A1 and 2003/0203210 A1, incorporated by reference. Additionally, Beneq deposits hermetic ceramic layers using atomic layer deposition (ALD) on polymer substrates. Another example is a film produced by Tera-Barrier Films Pte Ltd. that uses nanoparticles in combination with silicon oxide to form an impermeable layer. See, U.S. Pat. No. 6,737,753, incorporated by reference. These films are examples of barriers that may be applied to a polymer film to make it more impermeable. To form a hermetic reservoir, one of these coatings could be applied to a polymer capsule containing the API. Alternatively, the solid form API could itself be the structural substrate that is directly coated with a barrier polymer and then a subsequent impermeable layer. The API can be coated with conventional tablet polymer coatings such as copovidone or non-conventional polymers. The requirements on the coating are that it be thermally and mechanically stable to the deposition process. This configuration has the advantage of minimizing the reservoir volume.

F. Bioerodible, Hermetically Coated Reservoirs

In some embodiments, a drug delivery device has a reservoir that is both bioerodible and hermetic. Material selection is important for a bioerodible, hermetic reservoir. For example, polymer materials may be bioerodible but are not hermetic. In fact, the mechanism by which many polymers bioerode requires that water to be present, such as in hydrolysis. On the other hand, ceramic and glass materials such as silicon oxide and silicon nitride can be hermetic. Additionally, silicon oxide and silicon nitride are also known to dissolve when placed in the body for long periods of time. See, Sara Lipka, John Maloney, "Biostability of Materials for an Implanted Drug Delivery Device," Annual Meeting—Society for Biomaterials in Conjunction with the International Biomaterials Symposium (2006); also, John Maloney, Sara Lipka, and Samuel Baldwin, "In Vivo Biostability of CVD Silicon Oxide and Silicon Nitride Films," Materials Research Society Symposium Proceedings, Vol. 872, 279-284 (2005).

In a preferred embodiment, a solid drug formulation is coated with a bioerodible polymer. Next, one or more thin layers (each layer being 0.01 micron to 10 microns thick) of silicon oxide or silicon nitride is deposited on the polymer coating using deposition methods such as e-beam, sputtering, evaporation, or chemical vapor deposition. The layers of silicon oxide or silicon nitride may also be created using chemically deposited glass, such as spin on glass. The silicon oxide or silicon nitride material creates a hermetic barrier around the drug formulation and the bioerodible polymer coating.

The resulting structure of glass coated polymer can be used to create a device having bioerodible hermetic drug reservoirs. For example, multiple bioerodible hermetic reservoirs can be placed in an envelope structure and implanted into a tissue, such as the eye. It is understood by one skilled in the art that more than one layer of silicon oxide or silicon nitride may be deposited on a device, and that a variety of layer combinations using these materials at various thicknesses is possible. Alternatively, the silicon oxide or silicon nitride layers may be alternated with bioerodible polymer layers. Alternatively, the silicon oxides and silicon nitrides could also be deposited directly on the solid drug form, eliminating the need for an intermediate bioerodible polymer layer.

The device may be implanted in the eye (or other body compartment, such as the subcutaneous space) for as little as one month and for as long as a few years. The useful life of the implant will be determined by the rate at which the silicon oxide or silicon nitride dissolves into the body and the thickness or geometry of the coating. As long as enough silicon oxide or silicon nitride remains on the implant, the device will remain hermetic and water will not contact the bioerodible coating until the silicon oxide or silicon nitride is breached with a light irradiation (e.g., laser beam). Once the device is breached by light irradiation, water is allowed to pass through the outer silicon oxide or silicon nitride to contact the bioerodible polymer. As the bioerodible polymer begins to breakdown, the drug is allowed to come in contact with body fluids. In the case of an eye implant, the fluid would be the vitreous or the aqueous humor. The drug is then released from the reservoir at a rate that is determined by the formulation. Other reservoirs that have not been breached by light irradiation and that continue to have intact silicon oxide or silicon nitride layers will remain hermetic.

Over time, the silicon oxide and silicon nitride will dissolve into the body. When the silicon oxide and silicon nitride are thin enough to let water pass through, the reservoir may no longer be hermetic, even if the reservoir had not been breached by a laser. In all cases, the entire device and its contents are made of polymers, excipients, drugs, and oxides or nitrides that erode in the body so that at some point after implantation, all portions of the device have eroded.

G. Sealing Techniques

The DDD reservoirs described above can be hermetically sealed using a variety of techniques. In some embodiments, the DDD includes a hermetic seal formed between and joining the structural elements that form the shell or low-permeability barrier. In some embodiments, the hermetic seal is the product of a chemical reaction between the one or more shell materials. In some embodiments, the hermetic seal is formed by localized heating effective to fuse together adjacent surfaces of one or more shells. In some embodiments, the hermetic seal is formed by a welding process to directly melt, mix, and bond the adjacent surfaces. In some embodiments, the hermetic seal is formed by localized resistive heating using a resistor patterned on one or more of the shell pieces. In some embodiments, the hermetic seal is formed by solid state mixing or scrubbing of the interfaces as is the case in ultrasonic welding or cold welding. In some embodiments, the hermetic seal comprises a metal gasket mechanically deformed around a shell or reservoir opening. In some embodiments, either of the one or more shell materials comprises the gasket and the other shell material comprises a plurality of rigid, stress-concentrating structures. In some embodiments, the stress-concentrating structures comprise a plurality of ridge members and valleys between them. In some embodiments, the ridge members are tapered. In some embodiments, the shell comprises a gold foil. In some embodiments, the gasket is loaded in compression using mechanical fasteners or welding. In some embodiments, the hermetic seal comprises a weld between the one or more shell materials. In some embodiments, the hermetic seal comprises a metal or an alloy. In some embodiments, the hermetic sealing materials comprise a silicate glass. In some embodiments, the hermetic seal comprises a eutectic bond. In some embodiments, the eutectic bond comprises a eutectic composition comprising indium or tin. In some embodiments, the eutectic bond comprises a eutectic composition selected from the group consisting of gold/silicon, gold/germanium, gold/tin, gold/indium, lead/tin, lead/indium, and platinum/silicon. In some embodiments, the hermetic sealing materials comprise a metal selected from the group consisting of gold, tin, indium, platinum, titanium, palladium, tantalum, aluminum, stainless steel, and combinations thereof. In some embodiments, the hermetic material comprises aluminum oxide, aluminum nitride, silicon dioxide, or silicon nitride. In some embodiments, the hermetic seal comprises a metal seal and a layer of a biocompatible polymeric material. In some embodiments, the polymeric material comprises a poly(hydroxy acid) or poly(lactic acid), an epoxy, a polyurethane, a latex, a silicone, or a parylene. In some embodiments, the shell comprises a glass or ceramic substrate having a metal layer thereon. In some embodiments, the metal layer is deposited on the glass or ceramic substrate. In some embodiments, the metal layer is a metal foil bonded directly to the glass or ceramic substrate. In some embodiments, the metal foil comprises gold. In some embodiments, the shell materials both comprise a gold layer, the two gold layers being bonded together to form the hermetic seal. In some embodiments, the devices further comprise a plurality of reservoir caps sealing the reservoirs at an open end of a reservoir shell and features for selectively disintegrating the reservoir caps to release or expose the reservoir contents. In some embodiments, the open end of the reservoir comprises metal traces and a hermetic sealing substrate is welded onto the metal traces. In some embodiments, the reservoir cap comprises a metal foil. In some embodiments, the hermetic sealing substrate comprises a multi-layered structure including a glass layer anodically bonded to the reservoir shell, the glass layer having apertures in communication with the reservoirs. In some embodiments, the multi-layered structure further comprises a patterned metal layer anodically or eutectically bonded to the glass layer on the side distal to the reservoir shell. In some embodiments, the patterned metal layer has apertures in communication with the reservoirs and with the apertures in the glass layer. In some embodiments, the multi-layered structure further comprises a metal foil laser welded to the patterned metal layer on the side distal the glass layer, the metal sheet sealing the space defined by the reservoirs and apertures.

2. Laser Activation

Laser-activated reservoirs facilitate non-invasive release of an API directly to the tissue being treated (e.g., a posterior chamber or vitreous portion of the eye). In addition to being non-invasive, laser activation allows for multiple dosing from a single, multi-reservoir DDD.

The DDDs described above are capable of releasing an API payload when triggered by a pulse of optical radiation. In some embodiments, the optical radiation source is a focused laser. In some embodiments, the DDD includes a low-permeability barrier element with an optically absorbing material or incorporated structure to produce localized energy absorption. In some embodiments, the barrier element has a wall thickness that is substantially thinner and more mechanically fragile than other portions of the barrier element. In some embodiments, the thinner section has an optically absorbing material incorporated in it. In some embodiments, the absorbing material has a high optical absorption coefficient at a wavelength appropriate to a laser device to be controlled by a user for release of the chemical substance.

In some embodiments, the reservoir is made from a shell material with mechanical properties and thickness chosen to allow the shell wall to be substantially more fragile than other portions of the DDD. In some embodiments, the end caps or bottom pieces of the individual shell segments are sufficiently thick to allow for low thermal resistance between the cavities and the outer surface of the end caps or bottom pieces. In some embodiments, at least one of the end caps has a low thermal resistance between the interior of the barrier and the outer surface of the cap.

A. Laser Activation of Metalized Reservoirs

In general, laser activation can be facilitated by providing an area or target on the DDD that is capable of being breached using a pulse or series of pulses of laser radiation. In some cases, the shell walls of the reservoir are able to be breached if sufficiently thin and the walls are capable of absorbing sufficient energy from a laser pulse. In other cases, the laser-activation site is a small area of the shell wall that has been treated or adapted to facilitate a laser-activated breach. The techniques described below can be used to facilitate laser activation of many of the metalized reservoirs described above.

Referring to FIG. 12 as an exemplary embodiment, laser-activation sites 18 represent areas where laser energy may be applied to penetrate, perforate, or open the wall of an individual shell segment forming a drug reservoir. For some metal materials, absorption of optical energy by long duration laser pulses is intrinsically low while the thermal conductivity is relatively high. The combination of these facts makes it difficult to damage even thin sections of some metals by moderate to low intensity lasers, such as the 532 nm photocoagulators and other visible wavelength pulsed-CW lasers used in retinal therapy. Minimizing the metallic cross-section of the shell wall, provides a laser-activation site that allows for easier laser perforation. Thicknesses below 10 μm, and preferably as thin as 1 μm are desirable. Uniformly thin cross-sections can be difficult to fabricate and may compromise the shell structural integrity. Creating a limited zone with thinner cross-section while maintaining a thicker cross-section of the overall device allows the segment to have reasonable mechanical integrity.

The addition of a strong laser absorber material to the activation site allows for efficient coupling of laser energy into the metal via thermo-mechanical, thermal, acoustic, mechanical, or other means. Absorbers may be organic or inorganic films and can be deposited in a variety of ways. Examples include vacuum deposition of a metallic coating (e.g., Titanium), dip coating in or spraying on a carbon-impregnated polymer film, or organic adhesion layers (e.g., thiol chemistries on gold) chemically conjugated with an absorbing biocompatible dye (e.g., fluorescein or the naturally occurring pigment, such as the melanins). In addition, increasing the surface roughness of the underlying substrate or the deposited layer may increase laser light absorption. The result, in some cases, is that modest laser intensities can be applied to produce local destruction of the thin metal section and perforation of the drug reservoir (segment wall).

Alternatively, the metal surface may be treated to produce an absorbing surface, such as an oxidized surface, or other means of physically or chemically modifying the local surface. Alternatively, the entire outer surface of a segment may be covered with or bonded to a film, such as a polymer film, in which the laser absorption and transfer of metal-damaging energy is accomplished.

A laser absorbing activation site also enables laser energy to be directed and the size and location of the opening to be controlled. The location and size of the site allows protection of the API payload from potential thermal, optical, or mechanical force degradation associated with the laser activation mechanism. That is, the activation site can be located away from the API payload.

Another alternative is to use a higher power laser to directly ablate relatively thick layers of barrier wall material. The Nd:YAG nanosecond lasers used in ophthalmic secondary cataract laser surgery, for example, have been used to perforate representative thicknesses of gold foil which may be used to construct a reservoir segment. The use of these higher intensity pulsed lasers may eliminate both the requirement to have very thin cross-sections of reservoir material and the requirement to incorporate a laser absorbing compound; these very short pulse lasers ablate through non-linear processes and may not depend for their interaction on the linear absorption character of the material.

Laser activation can also be used to trigger multiple or staged API release. Referring to FIG. 14, a DDD can be constructed with laser-activation site 18 on a shell segment connected to an adjacent shell segment having a passive barrier. On laser activation at the site 18, the API in the first segment 50 elutes through the opening created at site 18, providing an initial dose of drug, and exposes the cavity interior of reservoir 50 to fluid or other biological substances, which causes the polymer material composing the passive barrier 80 to erode over a prescribed time. After the passive barrier 80 has been breached, biologic substance (fluid) gains ingress to the cavity of the second segment 52 through opening 70, causing the API in the cavity of 52 to elute into the first reservoir segment 50 and therefore from the DDD through the perforation at the location of site 18.

B. Laser Activation of an Ampule Reservoir

Referring to FIG. 16, laser-activation sites 18 are areas where laser energy may be applied to penetrate, perforate, fracture, or open the glass wall of an individual micro-ampule forming a drug reservoir. Absorption of optical energy by long duration laser pulses in glass is typically very low. Adding a suitable laser absorbing material to the glass wall allows for the efficient absorption of laser energy at the desired activation site. The material, such as carbon-containing pigment or a pigmented polymer film, may be placed on the interior or the exterior of the glass wall. Alternatively, the glass itself may be formed with an absorber, such as the types of optically absorbing glasses available from Schott Glass (examples: RG1000 visible light absorbing glass). Damage to a thin wall of glass requires significantly less thermal energy than metal or polymer ablation mechanisms for the same wall thickness. The glass may be fractured under thermo-mechanical stress, rather than vaporized or damaged through other energy-intensive state change mechanisms. Additionally, glass is particularly useful as a low energy laser damage material, because once an absorbing material has been added or coupled to the glass, the very low thermal conductivity of glass allows for the concentration of energy and thermal stress. Wall thicknesses below 100 microns are particularly fragile and susceptible to localized laser damage, which is desirable.

Referring to FIGS. 17 and 18, if tube 60 is a non-optically transparent superstructure, features 72 such as perforations in the tube may be created in advance of assembly to allow laser access to the laser-absorbing structures 18. Finally, the entire superstructure tube 60 may be intrinsically optically absorbing, in which the laser absorption and transfer of glass-damaging energy is accomplished (not pictured).

C. Laser Activation of a Metal-Clad Polymer Reservoir

Metal-clad polymer reservoir arrangements may reduce accident activation of both drug doses and laser damage to the delayed-release barrier while allowing targeting of the reservoir for any axial rotation of the device. That is, the external black or light-absorbing zones are visible no matter how the device is rotated, but the internal divider zone is not sensitive to laser-activation.

Laser absorption occurs in the structural layer by appropriate dopants or in layer(s) applied on either surface of the structural layer, or on the outer surface of the hermetic metal sealing layer. The patterning and design of the absorbing areas or zones can be created to allow laser activation from any rotation angle of the device. It is desirable to avoid designing the implant for laser absorption over 100% of the surface. By this means, it is possible to avoid inadvertent laser activation of the area near the delay-release film barrier, the hermetic seal/cold-weld boundary, and the area where two separate API volumes come close together.

Along the strip of device surface where the delayed-release polymer is attached to the outside shell of the device, there is no absorptive material. This assures that the laser opens only one discrete chamber within a device and that both chambers within the device cannot be accidentally opened simultaneously.

D. Indirect or Non-Laser Breach of a Reservoir

FIG. 27 depicts a method of opening a reservoir without requiring the laser to directly breach the reservoir walls. In this configuration, a low temperature shape memory alloy (SMA) 410 is wrapped around the circumference of a reservoir 400. The SMA 410 is comprised of strips with a sharp end 412 as shown in FIG. 27. The ends 412 of the shape memory alloy 410 are sharp and folded towards the end of the reservoir 400 as assembled. By irradiating any individual strip of the SMA 410 one strip or several strips may heat up above the material transition temperature, causing a contraction. This contraction causes the sharp end 412 of the SMA 410 to pierce the end of the reservoir 400, thus releasing its contents. Once the irradiation is terminated, the SMA 410 would return to its elongated shape, thus removing the sharp ends 412 from the pierced sites of one end of the reservoir 400. The advantage of this technique may be that less total energy is required than that which would be required to breach the reservoir sidewalls directly with a laser. In addition, the contents of the reservoir 400 would be protected from direct exposure to the laser or any debris caused by the laser's interaction with the reservoir sidewall.

Figure 28:
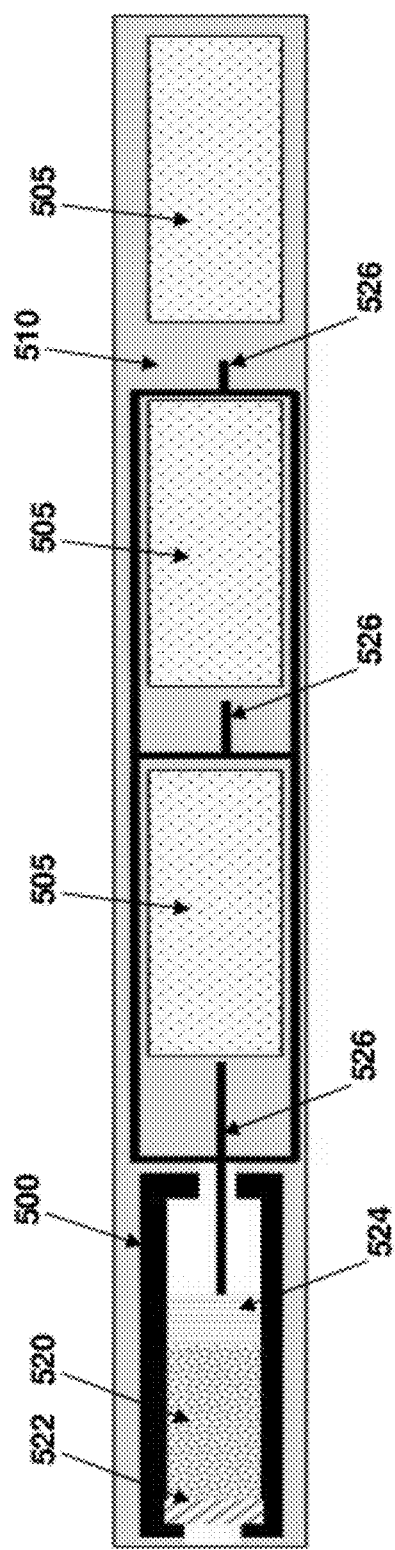
FIG. 28 depicts an embodiment for non-laser breach of a reservoir.

FIG. 28 depicts a device that does not require any laser interaction to deliver doses on a regular schedule. FIG. 28 depicts an osmotic engine 500 and drug filled reservoirs 505 are mounted to a base substrate 510. In this configuration an osmotic agent 520 is diluted by an aqueous solution through a semipermeable membrane 522. This dilution causes a volume increase between the semipermeable membrane 522 and a piston 524, thus displacing the piston 524 towards the reservoir tubes 505. Attached to the piston at regular intervals between reservoirs 505 are piercing elements 526. As shown in FIG. 28, these piercing elements 526 are of different lengths; they become progressively shorter from left to right. Thus, as the piston 520 displaces at a constant velocity, the left most reservoir will be pierced first followed by the middle reservoir and finally the right reservoir in sequence. The time between releases can be controlled by the rate of the piston displacement, the length of the piercing elements, and the reservoir spacing.

3. Drug Elution

Controlled Release achieves a slow release of drug over an extended period of time. The system is capable of providing control at a constant drug level.

Sustained Release prolongs the release of drug over a period of time, but not necessarily at a constant drug level.

Pulsatile Release achieves an intermittent dose of drug, where a "drug holiday" between doses requires the efficacious circulating levels of drug in the body to drop below the therapeutic window.

Delayed Release achieves an intermittent dose of drug from one or more controlled release systems incorporated into one dosage form.

As explained above, a hermetically-sealed implant with multiple drug reservoirs can be implanted and subsequently activated with a laser. In some cases, laser activation is required for each individual reservoir.

The following discussion relates to an embodiment with two doses in a single reservoir. The interior of each reservoir in this embodiment contains two separate drug volumes (Dose 1 and Dose 2), separated by a non-hermetic barrier material or film. Designs employing more than 2 separate doses are obviously possible by extension. The barrier may be biodegradable or soluble, in such a manner that the barrier fails after a characteristic time of exposure to water, biological fluid, or other substance.

The reservoir is then capable of delivering two doses of drug substance for each single laser activation event. These two doses proceed sequentially, with the first dose released immediately following the laser activation, and the second dose following at a later time, determined by the design of the reservoir contents.

When the laser is activated and creates a hole in a device reservoir, a first drug dose (Dose 1) is delivered. The release rate mechanism for Dose 1 is based on two phenomena: flux through the orifice is governed by Fick's law $$J = -D(dC/dx), \qquad \text{Equation 1}$$

where J is the flux of drug out the orifice in the direction of decreasing concentration, D is the diffusion coefficient of the drug, and dC/dx is the concentration gradient; and release from the drug formulation matrix is governed by the Noyes-Whiney equation:

$$dC/dt = DS/Vh(C_s - C), \qquad \text{Equation 2}$$

where D is the diffusion coefficient of the drug, S is the surface area of the exposed solid (formulation matrix), V is the volume of solution, h is the thickness of the diffusion layer, $C_s$ is the saturation solubility of the drug, and C is the concentration of drug at time t.

For poorly-soluble drug substances (steroids like fluocinolone, dexamethasone), release from the implant will be dominated by the mechanism expressed in equation 2. For highly-soluble drug substances (antibodies, such as bevacizumab or ranibizumab), release from the implant will be dominated by the mechanism expressed in equation 1.

After Dose 1 of drug has been depleted from the opened chamber, the delayed-release barrier is exposed to fluid in the biological environment (for example, the vitreous humor of the eye). After a specified time period, the delayed-release polymer barrier is breached and fails to continue performing as a barrier, releasing Dose 2 from the second volume of drug.

The mechanism by which the delayed-release barrier performs is either through a surface erosion or bulk erosion of the barrier layer. In terms of bulk erosion, the delayed-release barrier mechanism can be described in steps 1) hydration of the polymer barrier material, 2) hydrolysis of the polymer bonds to create micropores through which water can migrate into the second chamber and drug molecules can diffuse out, resulting in an initial slow release of drug, and 3) complete erosion of the polymer layer, resulting in fast release of the drug by dissolution and diffusion mechanisms. The rate at which the polymer barrier may be designed to degrade may be one week to three months or longer. Alternatively, delayed release may be accomplished using a surface eroding barrier such as a polymer from the class polyanhydrides. In this case, micropores are not generally formed through the polymer prior to the nearly complete polymer dissolution. Note the delayed release barrier layer may be formed in a channel of a plug of non-erodible material, or may comprise the entire barrier plug or membrane.

The delayed-release polymer barrier's degradation may be designed for pulsatile delivery of each dose (e.g., after efficacious effect of Dose 1 is depleted) or sustained delivery (e.g., efficacious effect of Dose 1 is 50%, 75%, 90% of pharmaceutical acceptable level).

Dose 2 from the second chamber is governed by the same two release rate mechanisms as discussed above. Dose 2 may or may not be the same formulation of API as Dose 1.

The drug formulation may be comprised of solid state formulation (lyophilized cake, spray dried particles), a suspension in non-aqueous solvents (DMSO, EtOH, PG, PEG), or a suspension of API in a second solid state material (PEG, PVP, PG) or a non-aqueous solution (DMSO, EtOH, PG, PEG). The formulation may also be a compacted non-porous form to increase drug load per reservoir.

The DDD may include pharmaceutical compositions, comprising a solid matrix which comprises a drug and one or more excipient materials, dispersed throughout pores or interstices within the solid matrix, wherein the excipient material enhances stability of the drug while stored and subsequent dissolution upon administration.

In some embodiments, the rate or time of release of the drug molecules from one of the reservoirs is different from the rate or time of release of the drug molecules from another of the reservoirs. In some embodiments, the molecules for release comprise an anti-VEGF agent. In some embodiments, the anti-VEGF agent is released intermittently from the medical device. In some embodiments, the anti-VEGF agent is released monthly in intermittent doses of between about 50-500 µg. In some embodiments, the monthly intermittent doses are released over a period of twelve months or more. In some embodiments, a first excipient material is dispersed throughout pores or interstices within the solid matrix and a second excipient material occupies reservoir space not occupied by the first excipient material or the solid matrix, within each of the one or more reservoirs. In some embodiments, the one or more excipient materials, upon exposure to an environmental solvent for the drug, promote dissolution of the drug to enhance release of the drug from the reservoir. In some embodiments, the one or more excipient materials prevent aggregation or precipitation of the drug upon exposure to an environmental fluid to enhance release of the drug from the reservoir.

Enhanced dissolution may also be achieved by controlling the reservoir gas environment. For example, the reservoir may be vacuum sealed or sealed under a soluble gas blanket to increase the rate of solvent ingress following exposure of the dosage form.

In some embodiments, a visual indicator or dye is also included in the reservoir. The visual indicator or dye is also dispersed when the reservoir wall is breached, indicating that the API payload has been released. For a discussion of providing a visual indication of the rupture of a drug reservoir implanted within an eye, see U.S. patent application Ser. No. 12/910,572, filed Oct. 22, 2010.

4. Filling Reservoirs with a Active Pharmaceutical Ingredient

For some APIs (e.g., biomolecules), lyophilization of the formulation may be required. The present disclosure allows for dispensing of formulated API solution into the segment cavities, with subsequent lyophilization performed on the segments in parallel, prior to assembly into DDDs. Although FIGS. 24 and 25 depict metallic shell reservoirs, the same technique can be applied to fill and lyophilize an API in different types of reservoirs, including glass ampules with a metallic base or end cap.

Figure 24:
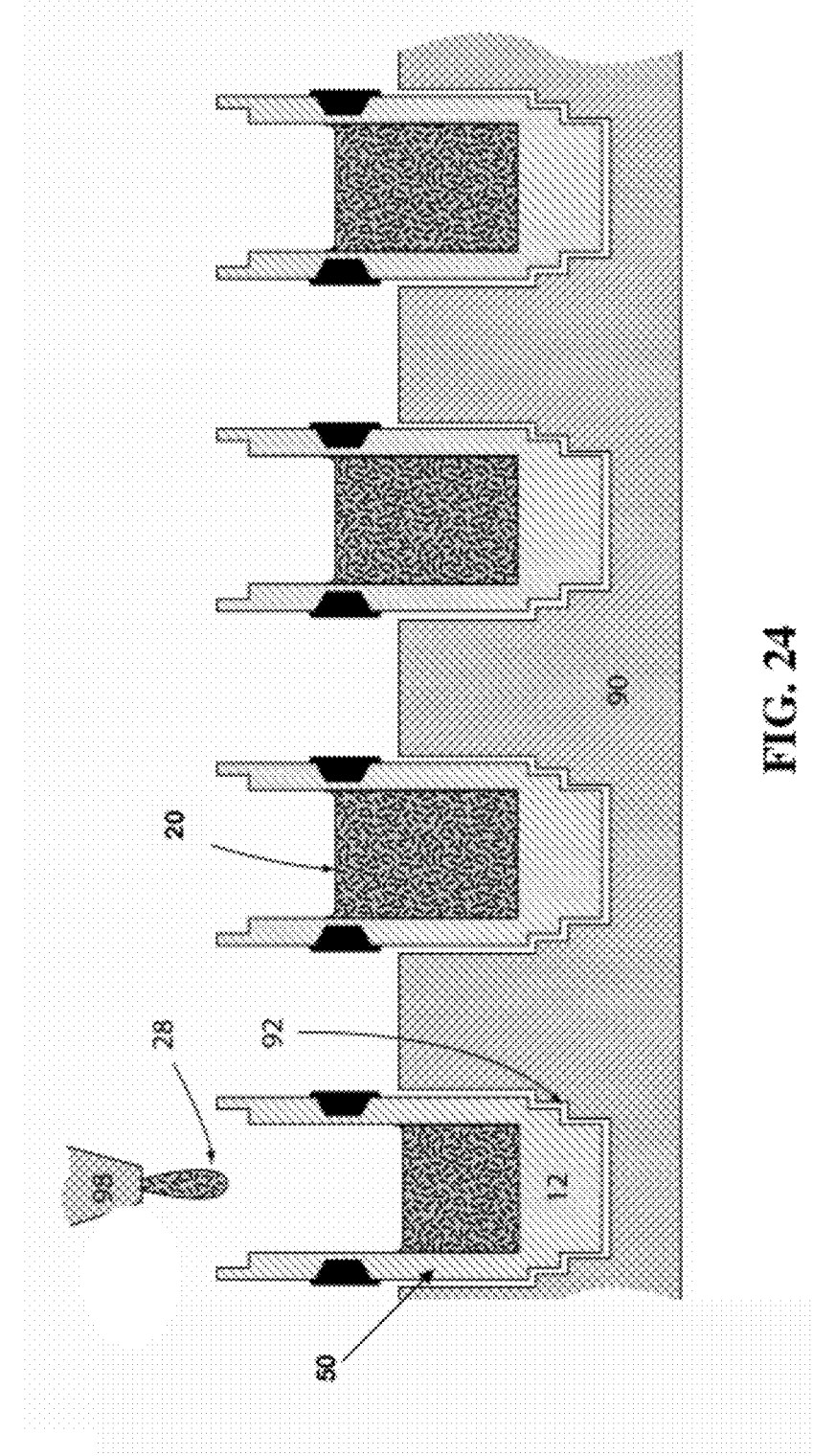
FIG. 24 depicts a series of individual reservoir shells mounted inside a fixture used to dispense and fill each reservoir shell with an API.

FIG. 24 illustrates an exemplary API-filling operation. A series of individual reservoir shell segments 50 are mounted in fixture 90 while an appropriate API 20 is dispensed through filling nozzle 98 into each reservoir. FIG. 24 depicts a filling operation in which the API is dispensed in a droplet 28. However, the reservoir can be filled with either solid or liquid form APIs using a variety of technologies. As shown in FIG. 24, pre-formed shell reservoirs 50 may be placed in a fixture suitable for micro-dispensing. Subsequently, individual therapeutic filling of doses into a reservoir 50 will require micro- or even nano-liter dispensing of the liquid or suspension.

After each shell reservoir 50 has been filled with API doses 20 loaded into the reservoirs by a (possibly sterile or aseptic) micro- or nano-dispensing technique, the tooling or fixture containing many filled segments may be placed in a lyophilization unit. Reservoir bottoms 12 are designed for high thermal conductivity. In reference to FIG. 25, temperature-controlled tooling fixture 90 can be designed to be in thermal conductance with the bottom 12 of individual reservoirs, resulting in low thermal resistance at interfaces 92. Low thermal resistance allows the lyophilization unit to efficiently control the temperature of the API formulation during the freeze dry cycle, a key aspect of lyophilization.

Figure 25:
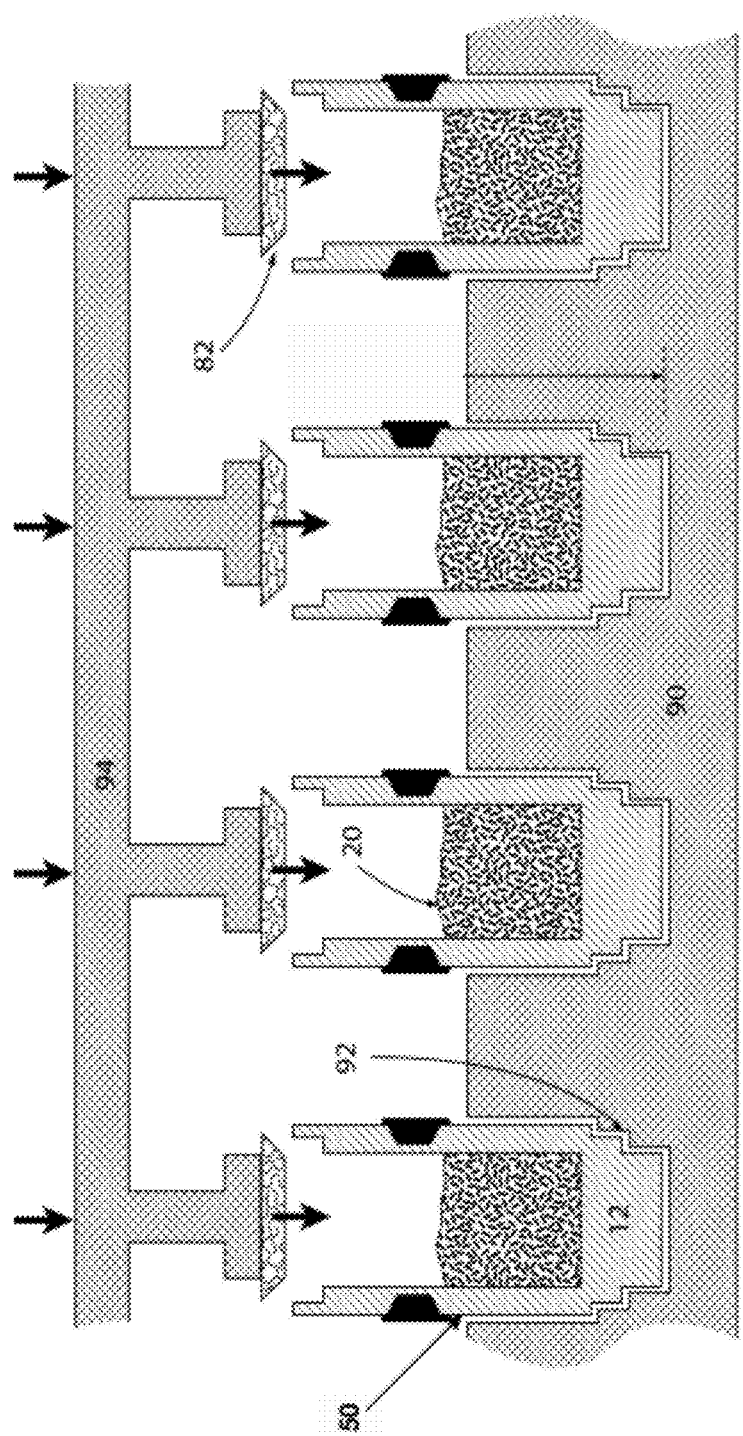
FIG. 25 depicts a series of filled individual reservoir shells in a fixture in which a second fixture is used to place protective caps to temporarily seal the contents of the reservoir shells prior to hermetic sealing.

FIG. 25 depicts an exemplary capping operation. In the event of an API payload that is sensitive to environmental degradation during handling or is sensitive to mechanical disturbance (such as a fine powder or delicate lyophilized cake), the API-filled, and possibly lyophilized, cavity may be capped with a biodegradable, soluble, or erodible material. See cap 82 in FIG. 25. Cap 82 will protect the delicate lyophilized "cake" during subsequent processing. As shown in FIG. 25, a fixture 94 incorporated into the lyophilizer or other API post-dispensing step may be employed to mechanically place these caps 82 in a simultaneous manner with a single actuator. After the lyophilization cycle is complete, but before segments are removed from the lyophilizer, cap 82 is lowered onto the filled segments. This non-hermetically seals each filled segment and allows them to be transported from the lyophilizer to the aseptic assembly station. The cap design may be compatible with standard shelf lyophilizing equipment with shelf lowering capability to insert rubber stoppers into standard parenteral lyophilization vials. The caps 82 are placed in such a manner at a sufficient depth in the cavities 30 that the subsequent hermetic sealing process is not interfered with. Protected reservoirs 50 may now be handled safely and assembled into a completed DDD.

Referring to FIG. 12, the cavity 30 of an individual metallic segment is filled with a suitable API 20 in advance of assembly of the complete DDD. The cavity 30 may be partially filled with a solid state API formulation, with a headspace at the top of the cavity. The head space may contain an inert and highly soluble gas or a vacuum allowing for rapid wet-up of the cavity 30 and hydration of the API 20 for efficient elution after laser activation of a reservoir in the completed and deployed DDD. Inert gases include elements from column VIII of the periodic table (e.g., Helium, Neon, Argon) and nitrogen. An example of a gas that is highly soluble in an aqueous liquid is carbon dioxide. Additionally, a partially-filled cavity with a headspace allows for laser activation of the reservoir with spatial separation of the laser-activation site 18 from the API 20.

Alternatively, the cavity 30 may be completely filled with a solid state API formulation (e.g., lyophilized API backfilled with non-aqueous solutions or polymers (e.g., polyethylene glycol (PEG), propylene glycol (PG), polyvinyl pyrrolidone (PVP), polyvinyl alcohol (PVA)) prior to assembly. The backfill of non-aqueous excipient also allows efficient hydration and delivery of the API upon laser activation.

Similar techniques can be applied to fill different types of reservoirs. For example, the technique can be applied to the dispensing of formulated API solution into micro-ampules that have been pre-sealed on one end. Subsequent lyophilization can be performed on the ampules in parallel, prior to sealing the second ends and subsequent assembly into DDDs.

Preformed and sterile ampule reservoir segments may be placed in a fixture suitable for micro-dispensing. Subsequently, individual doses for each micro-ampule may require micro- or even nano-liter dispensing of the liquid or suspension, potentially employing a sterile or aseptic fill technique. After each ampule has been filled, a tooling fixture containing many filled, open-ended ampules may be placed in a lyophilization unit.

Ampule bases 44 are designed for high thermal conductivity, and temperature-controlled tooling fixture (similar to the fixture 90 of FIG. 25) and the ends of individual micro-ampules are coupled with low thermal resistance at interfaces (similar to 92 of FIG. 25), which allows for the lyophilization unit to efficiently control the temperature of the API formulation during the freeze dry cycle, a key aspect of lyophilization.

After the lyophilization cycle is complete, but before segments are removed from the lyophilizer, a cap (similar to 82 in FIG. 25) is lowered onto the filled segments using a second fixture similar to 94 of FIG. 25. This effectively seals each filled segment and allows them to be transported from the lyophilizer to the aseptic assembly station. The cap design may be compatible with standard shelf lyophilizing equipment with shelf lowering capability to insert rubber stoppers into standard parenteral lyophilization vials. Caps 82 may be subsequently removed prior to hermetic sealing, or may be constructed from degradable or soluble material such as PVA that allows the caps to remain in place while the end cap 46 is hermetically sealed to complete the ampule.

A second fixture may be used to place degradable caps 82 inside the cavities while allowing for subsequent hermetic sealing of the ampule top end.

Figure 26A:
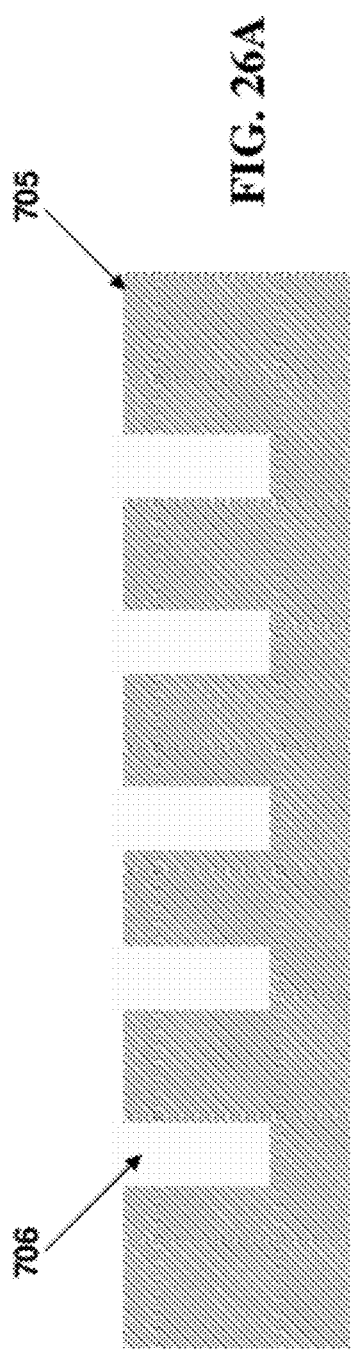
FIGS. 26A and 26B depict an electroforming method for forming and supporting reservoirs.
Figure 26B:
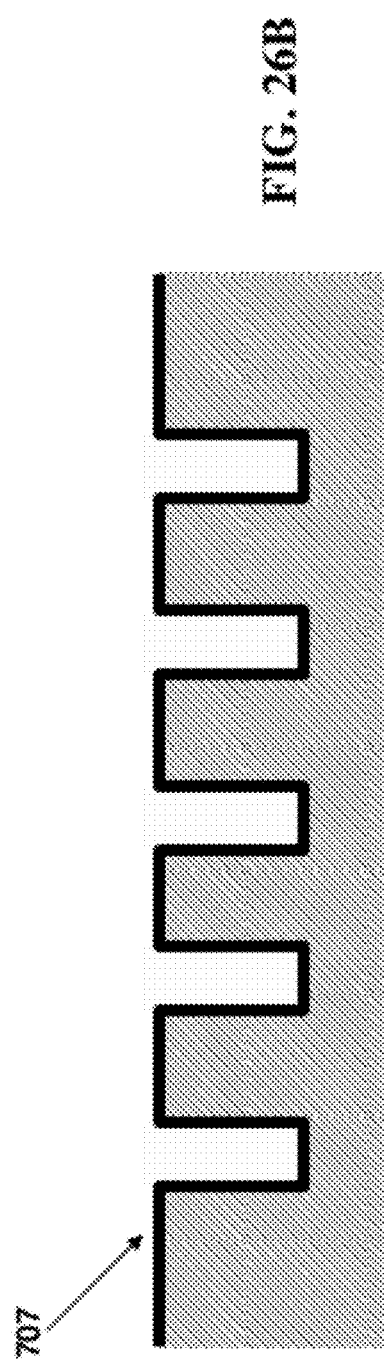

FIGS. 26A and 26B depict an alternative method of simultaneously forming and fixturing reservoirs using an electro-forming technique. In FIG. 26A, a fixture 705 is formed with holes 706 of a proscribed depth and diameter. The fixture 705 may be made from a conductive material such as a metal or metal alloy or may be a non-conductive material such as a ceramic, silicon, or glass. Holes 706 may be formed in a metal fixture using conventional machining techniques such as drilling, milling, laser drilling, or using plunge EDM. Holes 705 may be formed in Silicon using DRIE. Glasses and ceramics may be laser drilled or ground to form the holes 706. The APEX glass may be photo-defined and selectively etched. In some embodiments, of the fixture 705 is made from of a non-conductive material, a thin conductive metal may be vapor deposited onto the fixture 705 to make the surface conductive for the subsequent electroplating step (not shown).

FIG. 26B depicts an electroplated layer 707 that has been deposited forming a contiguous layer on the surface of the fixture 705. The preferred electrodeposited metal is gold and may be deposited in a range of 1 µm to 50 µm. This electrodeposited layer 707 forms the reservoirs which are now fully supported and bonded to fixture 705 for subsequent filling and sealing operations. Fixture 705 may remain for any of the appropriate filling and sealing operations previously described or the reservoirs may be separated from fixture 705 in a selective etching step prior to subsequent filling and sealing operations. A reservoir array may remain together or be separated into individual reservoirs prior to subsequent processing. Keeping the reservoirs bonded to fixture 705 may provide benefits in terms of heat transfer for lyophilization and allow greater thermal and mechanical loads during the sealing process. In addition, an array of reservoirs may provide manufacturing benefits by allowing parallel processing.

In some embodiments, the pharmaceutically active agent is selected from the group consisting of a peptide, protein (e.g., soluble receptor, antibody, etc.), and a gene therapy agent (e.g., polynucleotide, siRNA, RNAi, micro-RNA, etc.). In some embodiments, the extended delivery period is at least about 12-24 months, where each reservoir has an extended delivery period of at least 1, 2 and 3 months.

The DDDs described above can also be used for the storage and controlled release of a solid form of a drug comprising: providing a drug in dry, porous matrix form and combining with the drug matrix at least one excipient material which substantially fills the pores and interstices within the matrix to form a drug/excipient composite, wherein the drug/excipient composite, alone or in combination with another excipient material, substantially fills each of one or more reservoirs located in a body portion of a device for the storage and controlled release of the drug. In some embodiments, the dry, porous matrix form of the drug is first provided in the one or more reservoirs and then fluidized excipient material is added to the one or more reservoirs. In some embodiments, the dry, porous matrix form of the drug is formed by a method comprising: dissolving or dispersing a drug in a volatile liquid medium to form a first fluid; depositing a quantity of the first fluid into each of one or more reservoirs; and drying the quantity by volatilizing the volatile liquid medium to produce the dry, porous matrix of the drug in the one or more reservoirs. In some embodiments, the at least one excipient material is in a molten state when combined with the drug matrix. See also U.S. Pat. No. 7,488,316 and U.S. Pub. 2009/0142386 A1, and Elizabeth R. Proos, James H. Prescott and Mark A. Staples "Long-term Stability and In Vitro Release of hPTH (1-34) from a Multi-reservoir Array" *Pharmaceutical Research*, Volume 25, Number 6, 1387-1395 (Feb. 12, 2008).

To the extent that descriptions, definitions, and terms in material that is incorporated by reference conflicts with descriptions, definitions, and terms expressly included in this specification, the description, definition, and terms expressly included in this specification should govern.

What is claimed is:

1. An implantable drug delivery device comprising:
   a first shell element with a first enclosed cavity volume, wherein the first shell element forms a low-permeability barrier, and wherein the first shell element is configured to absorb light irradiation from a laser source, the light irradiation causing a breach in the first shell element;
   a first dose of an active pharmaceutical ingredient contained in the first enclosed cavity volume, wherein the first dose of the active pharmaceutical ingredient is released when the first shell element is breached;
   a second shell element with a second enclosed cavity volume, wherein the second shell element forms a low-permeability barrier; and
   a second dose of the active pharmaceutical ingredient contained in the second enclosed cavity volume, wherein the device releases time-delayed, multiple doses of the active pharmaceutical ingredient from a single laser activation of the first shell element.

2. The drug delivery device of claim 1, wherein the first shell element includes:
   a cup element having an open end and a flange portion; and
   an end cap element mechanically joined to the flange portion of the cup element so as to create the first enclosed cavity volume and to create a low-permeability seal preventing moisture from entering the first enclosed cavity volume.

3. The drug delivery device of claim 2, wherein the cup element and the end cap element are made from a metal material.

4. The drug delivery device of claim 3, wherein the end cap element is mechanically joined to the flange portion of the cup element using a cold welding technique and/or an ultrasonic welding technique.

5. The drug delivery device of claim 1, wherein the first shell element includes:
a tube element having two open ends, wherein the tube element is made from one of a glass, metal, or ceramic material;
a first end cap element mechanically joined to one of the open ends of the tube element;
a second end cap element mechanically joined to the other open end of the tube element,
wherein the tube element, first end cap element, and second end cap element create the first enclosed cavity volume, wherein the mechanical joining of the tube, first end cap element, and second end cap element creates a low-permeability seal preventing moisture from entering the enclosed cavity volume.

6. The drug delivery device of claim 1, wherein:
the first enclosed cavity volume is connected by one or more channels to the second enclosed cavity volume, the one or more channels allowing the transfer of the second dose of the active pharmaceutical ingredient from the second enclosed cavity volume to the first enclosed cavity volume.

7. The drug delivery device of claim 6, wherein a dissolvable, erodible or degradable barrier element is positioned to block the one or more channels and then to allow the transfer of the second dose of the active pharmaceutical ingredient from the second enclosed cavity volume to the first enclosed cavity volume and release of the second dose of active pharmaceutical ingredient through the breach in the first shell element after a period of time.

8. The drug delivery device of claim 1, further comprising:
a third dose of the active pharmaceutical ingredient contained in the drug delivery device;
a dissolvable, erodible or degradable barrier element is positioned between the first and third doses of the active pharmaceutical ingredient, wherein, the dissolvable barrier element is configured to be dissolved after a breach in the first shell element to allow the transfer of the third dose of the active pharmaceutical ingredient through the breach in the first shell element after a period of time.

9. The drug delivery device of claim 1, wherein the implantable drug delivery device has an insertion profile of less than 0.5 mm.

10. The drug delivery device of claim 1, wherein the implantable drug delivery device can be implanted by intravitreal injection.

11. The drug delivery device of claim 1, wherein said light irradiation comprises an application of energy from a laser, wherein the laser is selected from the group consisting of an argon ion laser, a Nd:YAG laser, a frequency-doubled Nd:YAG laser, a diode laser, a Nd:YLF laser, a frequency-doubled Nd:YLF laser, a krypton ion laser, a dye laser, and a helium-neon laser, a Raman-shifted Nd:YAG laser, a Nd:YV04 (vandate) laser, a frequency doubled Nd:YAG laser, a frequency-doubled Nd:YV04 (vandate) laser, a Raman-shifted Yb:fiber laser, a Yb:glass laser, and a Yb:YAG laser, a frequency-doubled Yb:fiber laser, a frequency-doubled Yb:glass laser, and a frequency-doubled Yb:YAG laser, and other non-linear optics crystal wavelength shifted lasers, including; frequency doubled VECSELs, sum and difference frequency mixed laser outputs from NIR lasers such as Nd:YV04, Nd:YAG, using such crystals as BBO, LBO, CLBO, KTP, KD*P, and RTA.

12. The drug delivery device of claim 1, wherein the active pharmaceutical ingredient is selected from the group consisting of anti-angiogensis agents, anti-inflammatories, anti-infectives, anti-allergens, cholingergic agonists and antagonists, adrenergic agonists and antagonists, anti-glaucoma agents, agents for cataract prevention or treatment, neuroprotection agents, anti-oxidants, antihistamines, antiplatelet agents, anti-coagulants, anti-thrombic agents, anti-scarring agents, anti-proliferatives, anti-tumor agents, complement inhibitors, decongestants, vitamins, growth factors, anti-growth factor agents, gene therapy vectors, chemotherapy agents, protein kinase inhibitors, small interfering RNAs, antibodies, antibody fragments, fusion proteins, litmus family compounds, and combinations thereof.

13. The drug delivery device of claim 12, wherein said anti-growth factor agent is an antivascular endothelial growth factor (anti-VEGF) agent.

14. The drug delivery device of claim 13, wherein said anti-VEGF agent is selected from the group consisting of aflibercept (VEGF trap), bevacizumab (AVASTIN), pegaptanib sodium (MACUGEN), and ranibizumab (LUCENTIS).

15. The drug delivery device of claim 1, wherein the first dose of the active pharmaceutical ingredient is protected from ingress of water or air when implanted in an eye of a patient for a period of at least 30 days.

16. An implantable drug delivery device comprising:
an active pharmaceutical ingredient;
a metallic substrate surrounding the active pharmaceutical ingredient forming a low-permeability barrier preventing moisture from entering the active pharmaceutical ingredient;
a polymer substrate bonded to the metallic substrate forming an external coating layer on an outer surface of the metallic substrate,
wherein the metallic substrate is configured to absorb light irradiation from a laser source, the light irradiation causing a breach in the polymer and metallic substrates, and
wherein the active pharmaceutical ingredient is released when the polymer and metallic substrates are breached.

* * * * *